US 7,745,414 B2
Jun. 29, 2010

(12) United States Patent
Eckhardt et al.

(10) Patent No.: US 7,745,414 B2
(45) Date of Patent: Jun. 29, 2010

(54) GLUCOPYRANOSYL-SUBSTITUTED BENZONITRILE DERIVATIVES, PHARMACEUTICAL COMPOSITIONS CONTAINING SUCH COMPOUNDS, THEIR USE AND PROCESS FOR THEIR MANUFACTURE

(75) Inventors: Matthias Eckhardt, Biberach (DE); Frank Himmelsbach, Mittelbiberach (DE); Peter Eickelmann, Mittelbiberach (DE); Achim Sauer, Ravensburg-Torkenweiler (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/674,839

(22) Filed: Feb. 14, 2007

(65) Prior Publication Data
US 2008/0058379 A1    Mar. 6, 2008

(30) Foreign Application Priority Data

Feb. 15, 2006   (EP) .................................. 06101711
May 3, 2006     (EP) .................................. 06113412
Nov. 27, 2006   (EP) .................................. 06124833

(51) Int. Cl.
C07H 1/00      (2006.01)
A01N 43/04     (2006.01)

(52) U.S. Cl. ..................... 514/23; 536/1.11; 536/18.7

(58) Field of Classification Search .................. None
See application file for complete search history.

(56) References Cited

U.S. PATENT DOCUMENTS

| 4,602,023 | A | 7/1986 | Kiely et al. |
| 4,786,023 | A | 11/1988 | Kiely et al. |
| 4,786,755 | A | 11/1988 | Kiely et al. |
| 6,414,126 | B1 | 7/2002 | Ellesworth et al. |
| 6,515,117 | B2 | 2/2003 | Ellesworth et al. |
| 6,627,611 | B2 | 9/2003 | Tomiyama et al. |
| 6,774,112 | B2 | 8/2004 | Gougoutas |
| 6,936,590 | B2 | 8/2005 | Washburn et al. |
| 7,169,761 | B2 | 1/2007 | Tomiyama et al. |
| 7,202,350 | B2 | 4/2007 | Imamura et al. |
| 7,371,732 | B2 | 5/2008 | Eickelmann et al. |
| 7,375,090 | B2 | 5/2008 | Himmelsbach et al. |
| 7,393,836 | B2 | 7/2008 | Eckhardt et al. |
| 7,417,032 | B2 | 8/2008 | Eckhardt et al. |
| 7,419,959 | B2 | 9/2008 | Eckhardt et al. |
| 7,579,449 | B2 | 8/2009 | Eckhardt et al. |
| 2002/0137903 | A1 | 9/2002 | Ellsworth et al. |
| 2003/0064935 | A1 | 4/2003 | Gougoutas |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2005/0065098 | A1 | 3/2005 | Fujikura et al. |
| 2005/0124555 | A1 | 6/2005 | Tomiyama et al. |
| 2005/0209166 | A1* | 9/2005 | Eckhardt et al. ............ 514/23 |
| 2006/0009400 | A1 | 1/2006 | Eckhardt et al. |
| 2006/0019948 | A1 | 1/2006 | Eckhardt et al. |
| 2006/0025349 | A1 | 2/2006 | Eckhardt et al. |
| 2006/0035841 | A1 | 2/2006 | Eckhardt et al. |
| 2006/0063722 | A1 | 3/2006 | Washburn et al. |
| 2006/0074031 | A1 | 4/2006 | Eckhardt et al. |
| 2006/0142210 | A1 | 6/2006 | Eckhardt et al. |
| 2006/0189548 | A1 | 8/2006 | Himmelsbach et al. |
| 2006/0234953 | A1 | 10/2006 | Himmelsbach et al. |
| 2006/0251728 | A1 | 11/2006 | Himmelsbach et al. |
| 2006/0258749 | A1 | 11/2006 | Eckhardt et al. |
| 2007/0004648 | A1 | 1/2007 | Himmelsbach et al. |
| 2007/0027092 | A1* | 2/2007 | Himmelsbach et al. ....... 514/23 |
| 2007/0049537 | A1 | 3/2007 | Eckhardt et al. |
| 2007/0054867 | A1 | 3/2007 | Eckhardt et al. |
| 2007/0073046 | A1 | 3/2007 | Eckhardt et al. |
| 2007/0249544 | A1 | 10/2007 | Himmelsbach et al. |
| 2007/0259821 | A1 | 11/2007 | Eckhardt et al. |
| 2009/0023913 | A1 | 1/2009 | Eckhardt et al. |

FOREIGN PATENT DOCUMENTS

| CA | 2 388 818 A1 | 4/2001 |
| CA | 2 494 177 A1 | 2/2004 |
| CA | 2 508 024 A1 | 6/2004 |
| CA | 2 508 226 A1 | 6/2004 |
| CA | 2 557 269 A1 | 9/2005 |
| CA | 2 557 320 A1 | 9/2005 |
| CA | 2 557 801 A1 | 10/2005 |
| CA | 2 573 777 A1 | 2/2006 |
| EP | 0 206 567 A2 | 6/1986 |
| EP | 1344780 A1 | 9/2003 |
| EP | 1 385 856 A0 | 2/2004 |

(Continued)

OTHER PUBLICATIONS

Adachi et al., "T-1095, a Renal Na+-Glucose Transport Inhibitor", Metabolism, vol. 49 (8), 2000, 990-995.*
Rachida Benhaddou et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Wolfgang Dohle et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Alois Fuerstner et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

(Continued)

Primary Examiner—Traviss C McIntosh, III
(74) Attorney, Agent, or Firm—Michael P. Morris; David A. Dow; Edouard G. Lebel

(57) ABSTRACT

Glucopyranosyl-substituted benzonitrile derivatives as defined herein, including the tautomers, the stereoisomers thereof, the mixtures thereof and the salts thereof. The compounds according to the invention are suitable for the treatment of metabolic disorders.

11 Claims, No Drawings

FOREIGN PATENT DOCUMENTS

| | | | |
|---|---|---|---|
| EP | 1224195 B | 5/2005 |
| EP | 1 553 094 A1 | 7/2005 |
| EP | 1 609 785 A1 | 12/2005 |
| JP | 58/164502 A | 9/1983 |
| JP | 62/030750 A | 2/1987 |
| JP | 11/124392 A | 5/1999 |
| JP | 2001/288178 A | 10/2001 |
| JP | 2003/511458 A | 3/2003 |
| JP | 2004/359630 A | 12/2004 |
| WO | 98/31697 | 7/1998 |
| WO | 01/27128 A1 | 4/2001 |
| WO | 01/74834 A1 | 10/2001 |
| WO | 02/064606 A1 | 8/2002 |
| WO | 02/083066 A2 | 10/2002 |
| WO | 03/099836 A1 | 12/2003 |
| WO | 2004/013118 A1 | 2/2004 |
| WO | 2004/052902 A1 | 6/2004 |
| WO | 2004/052903 A1 | 6/2004 |
| WO | 2004/063209 A2 | 7/2004 |
| WO | 2004/076470 A2 | 9/2004 |
| WO | 2004/080990 A1 | 9/2004 |
| WO | 2005/012326 A1 | 1/2005 |
| WO | 2005/012318 A2 | 2/2005 |
| WO | 2005/085237 A1 | 9/2005 |
| WO | 2005/085265 A1 | 9/2005 |
| WO | 2005/092877 A1 | 10/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Asanori Hatsuda et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Craig A Hutton et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Takehiko Iida et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

G. Erik Jagdmann, Jr; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Ja Seo Koo et al; 2-Pyridyl Cyanate: A Useful Reagent for he Preparation of Nitriles; Synthetic Communications (1996) vol. 26 No. 20 pp. 3709-3713; Marcel Dekker, Inc.

Takeshi Kuribayashi, et al; c-Glycosylated Aryl tins: Versatile Building Blocks for Aryl C-Glycoside Glycomimetics; J. Carbohydrate Chemistry (1999) vol. 18, No. 4 pp. 371-382.

Takeshi Kuribayashi, et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Takeshi Kuribayashi et al; Bis C-Glycosylated Diphenylmethanes for Stable Glycoepitope Mimetics; Syntletters (1999) vol. 6 pp. 737-740.

Sandrine Langle et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Mark Mclaughlin et al; Suzuki-Miyaura Cross-Coupling of Benzylic Phospahates with Arylboronic Acids; Organic Letters (2005) vol. 7 No. 22 pp. 4875-4878.

Ouri Neamati, et al, "Depsides and Depsidones as Inhibiton of HIV-1 Integrase: Dimvery of Novel Inhibitors Through 3D Database Searclung", J. Med. Chem., 1997, vol. 40, pp. 942-951.

Sabrina M. Nobre et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Akira Oku, et al; T-1095, An Inhibitor or renal $Na^+$-Glucose Cotransporters, May Provide a Novel Approach to Treating Diabetes; Diabetes (1999) vol. 48 pp. 1794-1800.

Richard J. Perner et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Michael Bech Sommer et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Lasslo Revesz et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Federica Stazi et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Rik R. Tykwinski; Evolution in the Palladium-Catalyzed Cross-Coupling of sp- and sp2-Hybridized Carbon Atoms; Angew Chemical International Edition (2003) vol. 42 pp. 1566-1568.

Kiichiro Ueta, et al; Long-Term Treatment with the $Na^+$-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Debra J. Wallace et al; Cyclopropylboronic Acid: Synthesis and Suzuki Cross-Coupling Reactions; Tetrahedron Letters (2002) vol. 43 pp. 6987-6990; Pergamon Press.

Song Xue et al; Zinc-mediated Synthesis of Alpha-C-Glycosided from 1,2-Anhydroglycosides; Synletters (2003) vol. 6 pp. 870-872.

International Search Report for PCT/EP2005/002618 mailed Jun. 30, 2005.

International Search Report for PCT/EP2006/061956 mailed on Jul. 5, 2006.

International Search report for PCT/EP2006/061957 mailed on Jul. 5, 2006.

International Search Report for PCT/EP2006/061520 mailed Jul. 26, 2006.

International Search Report for PCT/EP2006/062191 mailed Aug. 8, 2006.

International Search Report for PCT/EP2005/056806 mailed Dec. 27, 2006.

International Search Report for PCT/EP2006/066107 mailed Jan. 11, 2007.

International Search Report for PCT/EP2006/066347 mailed Mar. 7, 2007.

International Search Report for PCT/EP2006/065710 mailed Mar. 8, 2007.

International Search Report for corresponding PCT/EP2007/051411 mailed on May 2, 2007.

International Search Report for PCT/EP2007/054248 mailed on Jun. 18, 2007.

International Search Report for PCT/EP2006/064702 mailed on Jul. 26, 2007.

Notice of Allowance and Fee(s) Due dated Jan. 13, 2009 from U.S. Appl. No. 11/304,284 filed Dec. 15, 2005.

Non-Final Office Action dated Jun. 24, 2008 from U.S. Appl. No. 11/406,971 filed Apr. 19, 2006.

Non-Final Office Action dated Jun. 5, 2008 from U.S. Appl. No. 11/408,899 filed on Apr. 21, 2006.

Non-Final Office Action dated May 8, 2008 from U.S. Appl. No. 11/359,846 filed Feb. 22, 2006.

Response dated Nov. 5, 2008 to Non-Final Office Action dated May 8, 2008 from U.S. Appl. No. 11/359,846 filed Feb. 22, 2006.

Notice of Allowance and Fee(s) Due dated Feb. 3, 2009 from U.S. Appl. No. 11/359,846 filed Feb. 22, 2006.

Non Final Office Action dated Apr. 2, 2008 from U.S. Appl. No. 11/742,612 filed on May 1, 2007.

Response dated Sep. 25, 2008 to Non-Final Office Action dated Apr. 2, 2008 from U.S. Appl. No. 11/742,612 filed May 1, 2007.

Notice of Allowance and Fee(s) Due dated Jan. 2, 2009 from U.S. Appl. No. 11/742,612 filed May 1, 2007.

Notice of Allowance and Fee(s) Due dated Jan. 2, 2009 from U.S. Appl. No. 11/742,612 filed May 1, 2007.

U.S. Appl. No. 12/545,175 filed Aug. 21, 2009.

* cited by examiner

GLUCOPYRANOSYL-SUBSTITUTED BENZONITRILE DERIVATIVES, PHARMACEUTICAL COMPOSITIONS CONTAINING SUCH COMPOUNDS, THEIR USE AND PROCESS FOR THEIR MANUFACTURE

This application claims priority benefit from EP 06 101 711, filed Feb. 15, 2006; EP 06 113 412, filed May 3, 2006; and EP 06 124 833, filed Nov. 27, 2006, all of which are incorporated herein in their entirety.

The present invention relates to glucopyranosyl-substituted benzonitrile derivatives of the general formula I

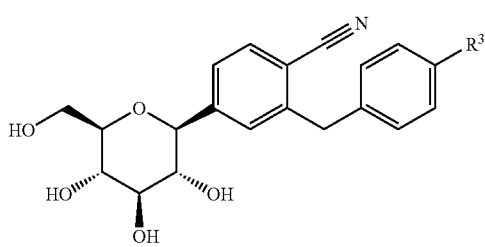

wherein the group $R^3$ is defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the sodium-dependent glucose cotransporter SGLT2 are proposed for the treatment of diseases, particularly diabetes.

Glucopyranosyl-substituted aromatic groups and the preparation thereof and their possible activity as SGLT2 inhibitors are known from the international application WO 2005/092877 and the publications cited therein.

AIM OF THE INVENTION

The aim of the present invention is to find new glucopyranosyl-substituted benzonitrile derivatives, particularly those which are active with regard to the sodium-dependent glucose cotransporter SGLT, particularly SGLT2. A further aim of the present invention is to discover glucopyranosyl-substituted benzene derivatives which have an enhanced inhibitory effect on the sodium-dependent glucose cotransporter SGLT2 in vitro and/or in vivo compared with known, structurally similar compounds and/or have better pharmacological or pharmacokinetic properties.

A further aim of the present invention is to provide new pharmaceutical compositions which are suitable for the prevention and/or treatment of metabolic disorders, particularly diabetes.

Other aims of the present invention will become apparent to the skilled man directly from the foregoing and following remarks.

OBJECT OF THE INVENTION

In a first aspect the present invention relates to glucopyranosyl-substituted benzonitrile derivatives of formula I

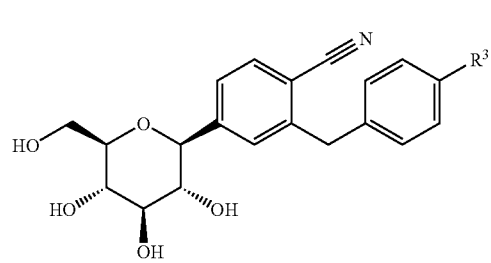

wherein
$R^3$ denotes hydrogen, fluorine, chlorine, bromine, iodine, methyl, ethyl, propyl, isopropyl, butyl, sec-butyl, iso-butyl, tert-butyl, 3-methyl-but-1-yl, cyclopropyl, cyclobutyl, cyclopentyl, cyclohexyl, difluoromethyl, trifluoromethyl, pentafluoroethyl, 2-hydroxy-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoro methyl-ethyl, 2-methoxy-ethyl, 2-ethoxy-ethyl, hydroxy, methyloxy, ethyloxy, isopropyloxy, difluoromethyloxy, trifluoromethyloxy, cyclobutyloxy, cyclopentyloxy, cyclohexyloxy, (S)-tetrahydrofuran-3-yloxy, (R)-tetrahydrofuran-3-yloxy, tetrahydropyran-4-yloxy, 1-acetyl-piperidin-4-yloxy, 2-methyloxy-ethyloxy, methylsulfanyl, methylsulfinyl, methlysulfonyl, ethylsulfinyl, ethylsulfonyl, trimethylsilyl and cyano, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl; including tautomers, stereoisomers thereof or mixtures thereof; and physiologically acceptable salts thereof.

The compounds according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or a physiologically acceptable salt thereof for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention or a physiologically acceptable salt thereof for preparing a pharmaceutical composition which is suitable for the treatment of one or more metabolic disorders.

In a further aspect the present invention relates to the use of at least one compound according to the invention or one of the physiologically acceptable salts thereof for preparing a pharmaceutical composition for preventing the degeneration of pancreatic beta cells and/or for improving and/or restoring the functionality of pancreatic beta cells.

In a further aspect the present invention relates to a use of at least one compound according to the invention or one of the physiologically acceptable salts thereof for preparing a pharmaceutical composition for preventing, slowing, delaying or treating diseases or conditions attributed to an abnormal accumulation of liver fat in a patient in need thereof.

This invention also relates to the use of at least one compound according to the invention or a physiologically acceptable salt thereof for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention or one of the physiologically acceptable salts thereof is incorporated in one or more inert carriers and/or diluents by a non-chemical method.

The present invention also relates to a process for preparing the compounds of general formula I according to the invention, characterised in that a) in order to prepare compounds of general formula I which are defined as hereinbefore and hereinafter,
a compound of general formula II

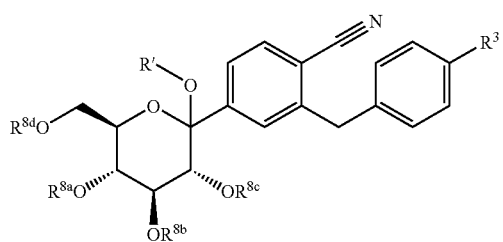

wherein
R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;
$R^{8a}$, $R^{8b}$,
$R^{8c}$, $R^{8d}$ independently of one another denote hydrogen or an allyl group, a benzyl group, a ($C_{1-4}$-alkyl)carbonyl, ($C_{1-4}$-alkyl)oxycarbonyl, arylcarbonyl, aryl-($C_{1-3}$-alkyl)-carbonyl and aryl-($C_{1-3}$-alkyl)-oxycarbonyl or a $R^aR^bR^c$Si group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and while alkyl, allyl, aryl and/or benzyl groups may be mono- or polysubstituted by halogen or $C_{1-3}$-alkoxy, and while benzyl groups may also be substituted by a di-($C_{1-3}$-alkyl)amino group; and
$R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups, preferably phenyl groups;
and wherein the group $R^3$ is defined as hereinbefore and hereinafter;
is reacted with a reducing agent in the presence of a Lewis or Brønsted acid, while any protective groups present are cleaved simultaneously or subsequently; or
b) in order to prepare compounds of general formula I, a compound of general formula III

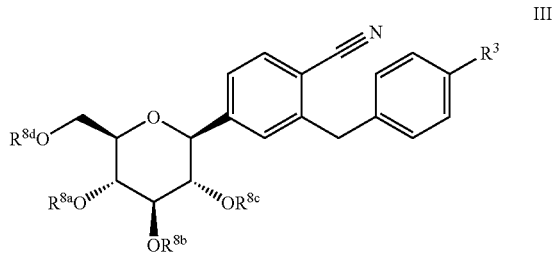

wherein $R^{8a}$, $R^{8b}$, $R^{8c}$, $R^{8d}$ and $R^3$ are defined as hereinbefore and hereinafter, with the proviso that at least one substituent selected from $R^{8a}$, $R^{8b}$, $R^{8c}$, $R^{8d}$ is not hydrogen;
the protective groups $R^{8a}$, $R^{8b}$, $R^{8c}$, $R^{8d}$ not being hydrogen are cleaved; and
if desired a compound of general formula I thus obtained is converted by acylation into a corresponding acyl compound of general formula I, and/or
if necessary any protective group used in the reactions described above is cleaved and/or
if desired a compound of general formula I thus obtained is resolved into its stereoisomers and/or
if desired a compound of general formula I thus obtained is converted into the salts thereof, particularly for pharmaceutical use into the physiologically acceptable salts thereof.

A further aspect of the present invention relates to novel intermediates as described in the reaction schemes and in the experimental part hereinafter.

DETAILED DESCRIPTION OF THE INVENTION

The aspects according to the present invention, in particular the compounds, pharmaceutical compositions and uses thereof, refer to glucopyranosyl-substituted benzonitrile derivatives of general formula I as defined hereinbefore and hereinafter, or derivatives thereof, including tautomers, stereoisomers or mixtures thereof, and physiologically acceptable salts thereof.

Preferably all hydroxyl groups of the β-D-glucopyranosyl group are unsubstituted or only the hydroxyl group O-6 of the β-D-glucopyranosyl group is substituted as defined. Preferred substituents are selected from among ($C_{1-8}$-alkyl)carbonyl, ($C_{1-8}$-alkyl)oxycarbonyl and phenylcarbonyl. Even more preferred substituents are selected from among acetyl, methoxycarbonyl and ethoxycarbonyl, in particular acetyl and ethoxycarbonyl.

The nomenclature in structural formulas used above and hereinafter, in which a bond of a substituent of a cyclic group, as e.g. a phenyl ring, is shown towards the centre of the cyclic group, denotes, unless otherwise stated, that this substituent may be bound to any free position of the cyclic group bearing an H atom.

The compounds according to the invention may be obtained using methods of synthesis known in principle. Preferably the compounds are obtained by the following methods according to the invention which are described in more detail hereinafter.

The glucose derivatives of formula II according to the invention may be synthesised from D-gluconolactone or a derivative thereof by adding the desired benzylbenzene compound in the form of an organometallic compound (Scheme 1).

Scheme 1: Addition of an Organometal Compound to a Gluconolactone

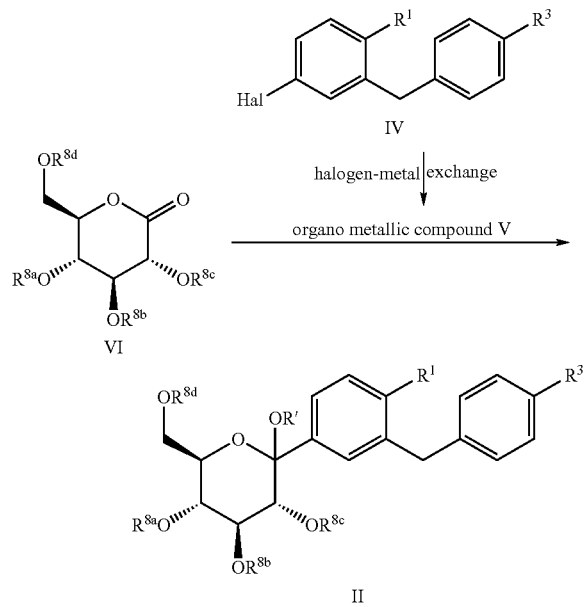

The reaction according to Scheme 1 is preferably carried out starting from a halogenated benzylbenzene compound of general formula IV, wherein Hal denotes chlorine, bromine, or iodine. $R^1$ in Scheme 1 denotes cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino functionality such as e.g. nitro. The Grignard or lithium reagent of benzylbenzene (V) may be prepared from the corresponding chlorinated, brominated or iodinated benzylbenzene IV either via a so-called halogen-metal exchange reaction or by inserting the metal into the carbon-halogen bond. The halogen-metal exchange to synthesize the corresponding lithium compound V may be carried out for example with an organolithium compound such as e.g. n-, sec- or tert-butyllithium. The analogous magnesium compound may also be generated by a halogen-metal exchange with a suitable Grignard reagent such as e.g. isopropyl- or sec-butylmagnesium bromide or chloride or diisopropyl- or di-sec-butylmagnesium without or in the presence of an additional salt such as e.g. lithium chloride that may accelerate the metalation process; the specific transmetalating organomagnesium compound may also be generated in situ from suitable precursors (see e.g. Angew. Chem. 2004, 116, 3396-3399 and Angew. Chem. 2006, 118, 165-169 and references quoted therein). In addition, ate complexes of organomagnesium compounds resulting from combining e.g. butylmagnesium chloride or bromide or isopropylmagnesium chloride or bromide and butyllithium, may be employed as well (see e.g. Angew. Chem. 2000, 112, 2594-2596 and Tetrahedron Lett. 2001, 42, 4841-4844 and references quoted therein). The halogen-metal exchange reactions are preferably carried out between 40° C. and –100° C., particularly preferably between 10° C. and –80° C., in an inert solvent or mixtures thereof, such as for example diethylether, dioxane, tetrahydrofuran, toluene, hexane, dimethylsulfoxide, dichloromethane or mixtures thereof. The magnesium or lithium derivatized compounds thus obtained may optionally be transmetalated with metal salts such as e.g. cerium trichloride, zinc chloride or bromide, indium chloride or bromide, to form alternative organometal compounds (V) suitable for addition. Alternatively, the organometal compound V may also be prepared by inserting a metal into the carbon-halogen bond of the haloaromatic compound IV. Lithium or magnesium are suitable elemental metals for this transformation. The insertion can be achieved in solvents such as e.g. diethylether, dioxane, tetrahydrofuran, toluene, hexane, dimethylsulfoxide and mixtures thereof at temperatures ranging from –80 to 100° C., preferably at –70 to 40° C. In cases in which no spontaneous reaction takes place prior activation of the metal might be necessary such as e.g. treatment with 1,2-dibromoethane, iodine, trimethylsilylchloride, acetic acid, hydrochloric acid and/or sonication. The addition of the organometal compound V to gluconolactone or derivatives thereof (VI) is preferably carried out at temperatures between 40° C. and –100° C., particularly preferably at 0 to –80° C., in an inert solvent or mixtures thereof, to obtain the compound of formula II. All foregoing reactions may be performed in air though execution under inert gas atmosphere such as argon and nitrogen is preferred. The metalation and/or coupling reaction may also be carried out in microreactors and/or micromixers which enable high exchange rates; for example analogously to the processes described in WO 2004/076470. Suitable solvents for the addition of the metalated phenyl group V to the appropriately protected gluconolactone VI are e.g. diethylether, dimethoxyethane, benzene, toluene, methylene chloride, hexane, tetrahydrofuran, dioxane, N-methylpyrrolidone and mixtures thereof. The addition reactions may be carried out without any further adjuvants or in the case of sluggishly reacting coupling partners in the presence of a promoter such as e.g. $BF_3 \cdot OEt_2$ or $Me_3SiCl$ (see M. Schlosser, Organometallics in Synthesis, John Wiley & Sons, Chichester/New York/Brisbane/Toronto/Singapore, 1994). Preferred definitions of the substituents $R^8$ in Scheme 1 are benzyl, substituted benzyl, allyl, trialkylsilyl, particularly preferably trimethylsilyl, triisopropylsilyl, allyl, 4-methoxybenzyl and benzyl. If two adjacent substituents $R^8$ are linked together, these two substituents are preferably part of a benzylideneacetal, 4-methoxybenzylideneacetal, isopropylketal or constitute a dioxane with 2,3-dimethoxy-butylene which is linked via the 2 and 3 positions of the butane with the adjacent oxygen atoms of the pyranose. The group R' preferably denotes hydrogen, $C_{1-4}$-alkyl, $C_{1-4}$-alkylcarbonyl or $C_{1-4}$-alkyloxycarbonyl, particularly preferably hydrogen, methyl or ethyl. The group R' is introduced after the addition of the organometallic compound V or a derivative thereof to the gluconolactone VI. If R' equals hydrogen or $C_{1-4}$-alkyl the reaction solution is treated with an alcohol such as e.g. methanol or ethanol or water in the presence of an acid such as e.g. acetic acid, methanesulfonic acid, toluenesulfonic acid, sulfuric acid, trifluoroacetic acid, or hydrochloric acid. R' may also be attached after preparation of the hydrogen compound II by reacting the anomeric hydroxyl group with a suitable electrophile such as e.g. methyl iodide, dimethyl sulfate, ethyl iodide, diethyl sulfate, acetyl chloride, or acetic anhydride in the presence of a base such as e.g. triethylamine, ethyldiisopropylamine, sodium or potassium or cesium carbonate, sodium or potassium or cesium hydroxide. The hydroxyl group can also be deprotonated prior to the addition of the electrophile with e.g. sodium hydride. During installing R' the protective groups $R^8$ may be cleaved if labile under the reaction conditions employed resulting in the corresponding protonated compound, i.e. compound II in which $R^8$ equals H.

The synthesis of haloaromatic compound of formula IV may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). More specifically, the use of transition metals and organo metal compounds for the synthesis of aromatic compounds has been detailed in different monographs (see e.g. L. Brandsma, S. F. Vasilevsky, H. D. Verkruijsse, Application of Transition Metal Catalysts in Organic Synthesis, Springer-Verlag, Berlin/Heidelberg, 1998; M. Schlosser, Organometallics in Synthesis, John Wiley & Sons, Chichester/New York/Brisbane/Toronto/Singapore, 1994; P. J. Stang, F. Diederich, *Metal-Catalyzed Cross-Coupling Reactions*, Wiley-VCH, Weinheim, 1997 and references quoted therein). The synthesis strategies described in the following provide a demonstration of this, by way of example. In addition, the aglycon part may also be assembled with the pyranose moiety already present using the same synthetic approaches.

Scheme 2: Synthesis of the Diarylketone Fragment

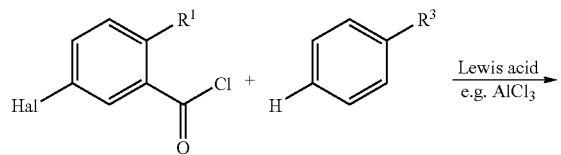

-continued

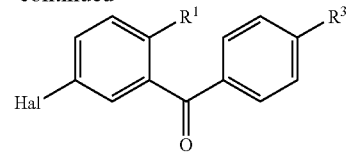

Scheme 2 shows the preparation of a precursor compound that may serve for the synthesis of the haloaromatic compound of formula IV starting from a benzoylchloride and a second aromatic group applying Friedel-Crafts acylation conditions or variations thereof. $R^1$ in Scheme 2 denotes cyano or a group that may be subsequently converted to a cyano group such as chlorine, bromine, carboxy, carboxylic ester, carboxamide or a derivative thereof, a protected or masked aldehyde function such as e.g. thioacetal or thiazole, or a protected or masked amino functionality such as e.g. nitro. This classic reaction has a wide substrate scope and is commonly carried out in the presence of a catalyst which is used in catalytic or stoichiometric amounts, such as e.g. $AlCl_3$, $FeCl_3$, iodine, iron, $ZnCl_2$, sulphuric acid, or trifluoromethanesulphonic acid. Instead of the benzoyl chloride the corresponding carboxylic acid, anhydride, ester or benzonitrile may be used as well. The reactions are preferentially carried out in chlorinated hydrocarbons such as e.g. dichloromethane and 1,2-dichloroethane at temperatures from −30 to 120° C., preferably at 30 to 100° C. However, solvent-free reactions or reactions in a microwave oven are also possible.

Scheme 3: Reduction of Diarylketones and Diarylmethanols to Diarylmethanes

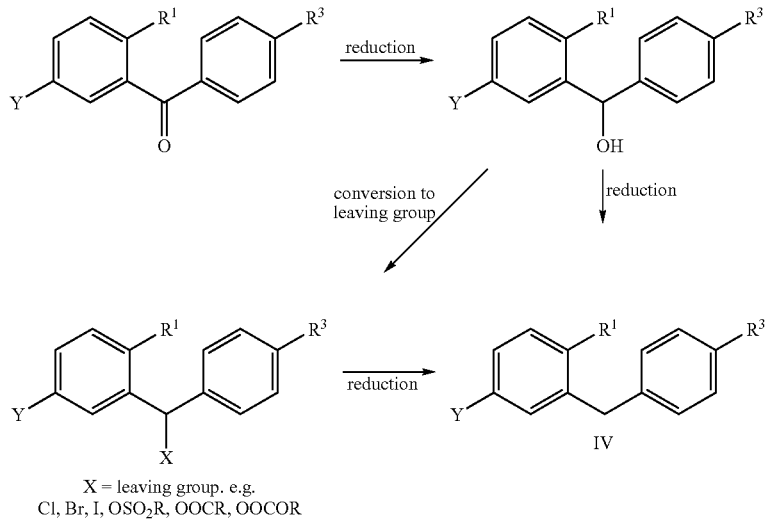

X = leaving group. e.g.
Cl, Br, I, $OSO_2R$, OOCR, OOCOR

Y = Cl, Br, I, or

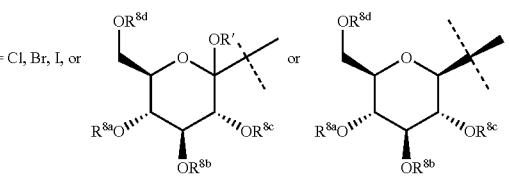

In Scheme 3 the substituent R denotes $C_{1-3}$-alkyl or aryl and $R^1$ cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino function such as e.g. nitro. Starting from the diarylketone or diarylmethanol the diarylmethane is accessible in one or two reaction steps. The diarylketone may be reduced to the diarylmethane in two steps via the corresponding diphenylmethanol or in one step. In the two-step variant the ketone is reduced with a reducing agent such as for example a metal hydride such as e.g. $NaBH_4$, $LiAlH_4$ or $iBu_2AlH$ to form the alcohol. The resulting alcohol can be converted in the presence of a Lewis acid such as for example $BF_3*OEt_2$, $InCl_3$ or $AlCl_3$ or Brønsted acid such as for example hydrochloric acid, sulfuric acid, trifluoroacetic acid, or acetic acid with a reducing agent such as e.g. $Et_3SiH$, $NaBH_4$, or $Ph_2SiClH$ to the desired diphenylmethane. The one-step process starting from the ketone to obtain the diphenylmethane may be carried out e.g. with a silane such as e.g. $Et_3SiH$, a borohydride such as e.g. $NaBH_4$ or an aluminum hydride such as $LiAlH_4$ in the presence of a Lewis or Brønsted acid such as for example $BF_3*OEt_2$, tris(pentafluorophenyl)borane, trifluoroacetic acid, hydrochloric acid, aluminum chloride or $InCl_3$. The reactions are preferably carried out in solvents such as e.g. halogenated hydrocarbons such as dichloromethane, toluene, acetonitrile, or mixtures thereof at temperatures of −30 to 150° C., preferably at 20 to 100° C. Reductions with hydrogen in the presence of a transition metal catalyst such as e.g. Pd on charcoal are another possible method of synthesis. Reductions according to Wolff-Kishner or variants thereof are also possible. The ketone is firstly converted with hydrazine or a derivative thereof, such as e.g. 1,2-bis(tert-butyldimethylsilyl)hydrazine, into the hydrazone which breaks down under strongly basic reaction conditions and heating to form the diphenylmethane and nitrogen. The reaction may be carried out in one reaction step or after isolation of the hydrazone or a derivative thereof in two separate reaction steps. Suitable bases include e.g. KOH, NaOH or KOtBu in solvents such as e.g. ethyleneglycol, toluene, DMSO, 2-(2-butoxyethoxy) ethanol or tert-butanol; solvent-free reactions are also possible. The reactions may be carried out at temperatures between 20 to 250° C., preferably between 80 to 200° C. An alternative to the basic conditions of the Wolff-Kishner reduction is the Clemmensen reduction which takes place under acidic conditions, which may also be used here. The alcohol function in diarylmethanol may also first be transformed into a better leaving group such as e.g. chloride, bromide, iodide, acetate, carbonate, phosphate, or sulfate; the subsequent reduction step to form the diarylmethane is widely described in the organic chemistry literature.

Scheme 4: Synthesis of Diarylmethane Unit and Possible Precursor Compounds thereof

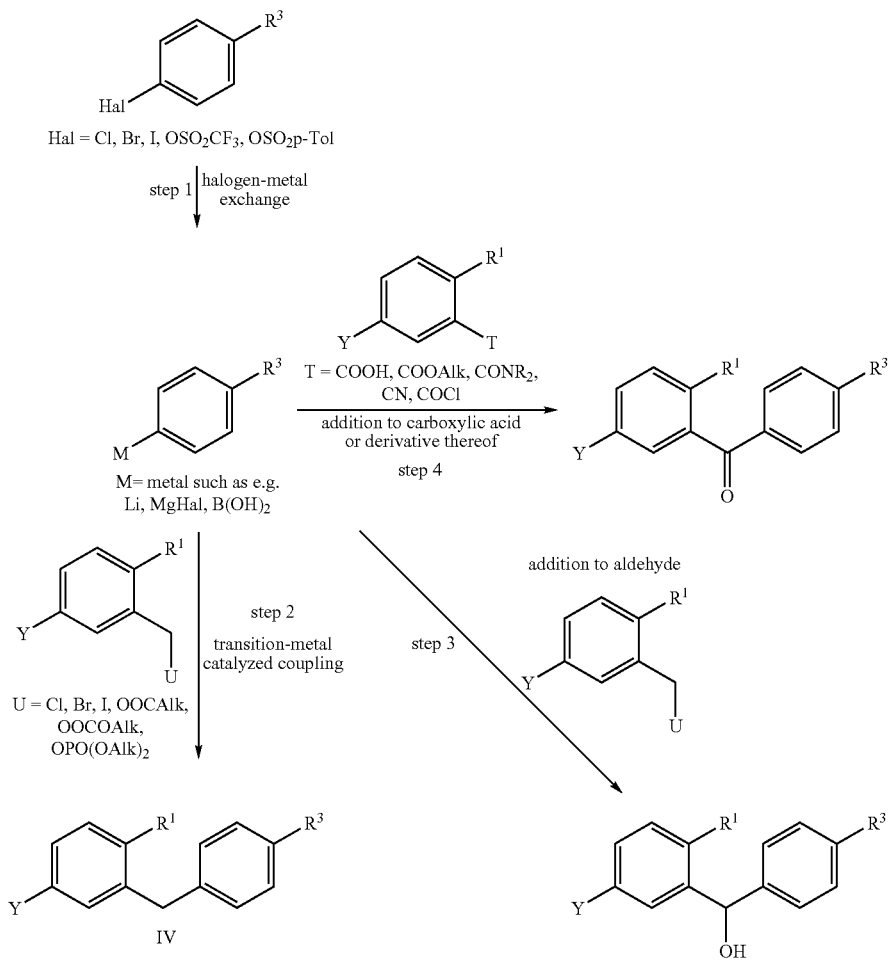

Y = Cl, Br, I, OSO$_2$CF$_3$, OSO$_2$p-Tol or 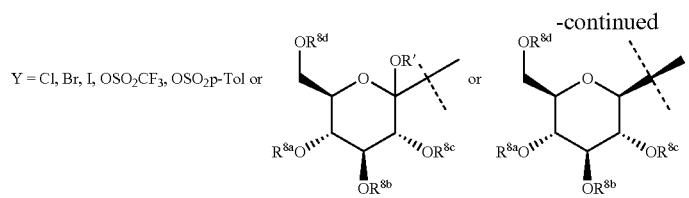

In Scheme 4 R$^1$ denotes cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino function such as e.g. nitro. The term "Alk" denotes C$_{1-4}$-alkyl and each substituent R is independently selected from each other from the group consisting of H, C$_{1-3}$-alkyl and C$_{1-3}$-alkoxy. Scheme 4 delineates the synthesis of diarylmethanes and possible precursor compounds thereof starting from a metalated phenyl group. Lithium or magnesium substituted aromatic compounds may be synthesized from chlorinated, brominated, or iodinated aromatics by a halogen-metal exchange reaction with e.g. butyllithium, isopropylmagnesium halogenide, or diisopropylmagnesium or by insertion of the elemental metal into the halogen-carbon bond. The corresponding boron substituted compound such as e.g. boronic acid, boronic acid ester, or dialkylarylborane, is accessible from these metalated phenyl groups by reaction with a boron electrophile such as e.g. boronic acid ester or a derivative thereof. In addition, the borylated aromatic compound may also be prepared from the corresponding halogenated or pseudohalogenated precursor and a diboron or borane compound through a transition metal, e.g. palladium, catalyzed reaction (see e.g. *Tetrahedron Lett.* 2003, p. 4895-4898 and references quoted therein). The lithium or magnesium substituted phenyl compounds add to benzaldehydes (step 3) and benzoic acids or derivatives thereof (step 4) such as benzoic acid esters, benzamides such as e.g. of the Weinreb type, benzonitriles, or benzoyl chlorides. These reactions may principally be conducted without an additional transition metal catalyst or transmetalation to another metal such as e.g. cerium, indium or zinc; sometimes the use of one of the latter alternatives is advantageous. Aryl boronic acids can be added to benzaldehydes by means of a rhodium catalyst furnishing the respective diarylmethanol (see e.g. *Adv. Synth. Catal.* 2001, p. 343-350 and references quoted therein). Moreover, arylboronic acids, esters thereof, dialkylarylboranes, or aryltrifluoroborates may be coupled with benzoyl chlorides mediated by a transition metal such as e.g. palladium, a complex or a salt thereof delivering diarylketones. Metalated phenyl groups can be reacted with benzyl electrophiles such as benzyl chlorides, bromides, or iodides affording diarylmethanes. Lithium or magnesium derivatized phenyl compounds are reacted favorably but not always necessarily in the presence of a transition metal such as e.g. copper, iron, or palladium (see e.g. *Org. Lett.* 2001, 3, 2871-2874 and references quoted therein). Transmetallation from lithium or magnesium to e.g. boron, tin, silicon, or zinc furnishes e.g. the corresponding aromatic boronic acids, stannanes, silanes or zinc compounds, respectively, that may undergo coupling with benzyl electrophiles, e.g. benzyl halogenides, carbonates, phosphates, sulfonates, or carboxylic esters. The reaction is conducted in the presence of a transition metal, e.g. palladium, nickel, rhodium, copper, or iron (see e.g. *Tetrahedron Lett.* 2004, p. 8225-8228 and *Org. Lett.* 2005, p. 4875-4878 and references cited therein).

Scheme 5: Introduction of the Cyano Moiety

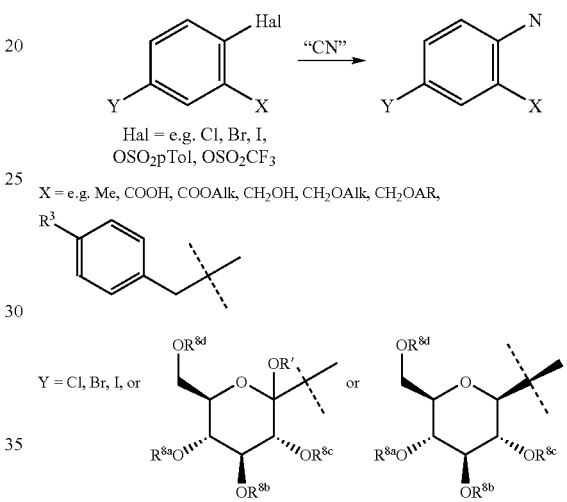

Hal = e.g. Cl, Br, I, OSO$_2$pTol, OSO$_2$CF$_3$

X = e.g. Me, COOH, COOAlk, CH$_2$OH, CH$_2$OAlk, CH$_2$OAR,

Y = Cl, Br, I, or

Scheme 5 displays possible pathways to attach the cyano residue to the central phenyl group at various stages of the synthesis of the target molecules. The cyano group may be introduced via a transition metal mediated coupling reaction of an appropriate cyano source such as e.g. sodium, potassium, zinc or copper cyanide with a halogenated or pseudohalogenated phenyl group. Suitable catalysts may be derived from transition metals such as e.g. palladium, rhodium, nickel, iron or copper that may be used in elemental form such as e.g. palladium on carbon, as salts such as e.g. palladium chloride, bromide or acetate or complexes with e.g. phosphines such as e.g. triphenylphosphine, tri-tert-butylphosphine or dppf or alkenes such as e.g. dibenzylideneacetone. The active catalyst may be generated in situ or prior to the addition to the reaction mixture. Additives such as e.g. zinc as element or salt may be advantageous (see *Tetrahedron Lett.* 2005, 46, 1849-1853 and *Tetrahedron Lett.* 2005, 46, 1815-1818 and references quoted therein). Reacting the corresponding zinc, magnesium or lithium compound, accessible from the chlorinated, brominated or iodinated compound via a halogen metal exchange reaction or by insertion of the respective metal into the halogen bond, with a cyano electrophile such as e.g. p-tolylsulfonyl cyanide, cyanogen bromide or 2-pyridyl cyanate is another viable approach to install the cyano functionality (see e.g. *Synth. Commun.* 1996, 3709-3714 and references quoted therein).

Scheme 6: Introduction of the cyano residue from aldehyde or carboxylic acid derivative

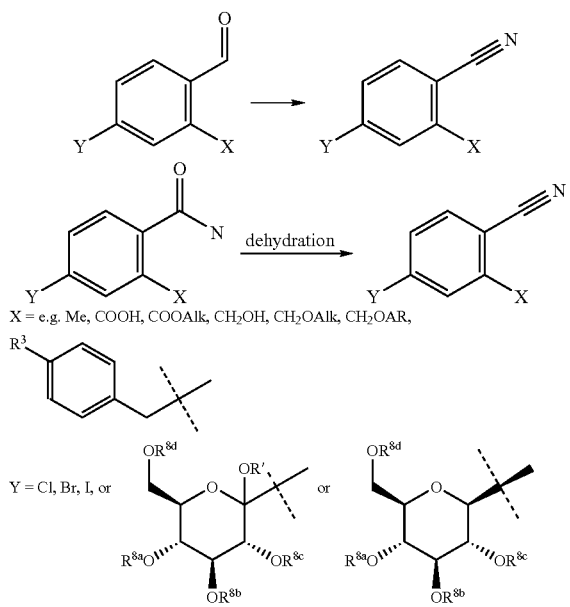

An alternative introduction of the cyano group is the synthesis starting from aldehyde or carboxamide (Scheme 6). The aldehydic function itself can be introduced as such, protected, or masked. Popular protective groups for the aldehyde function are acetals, but other protective groups may be used as well (see T. W. Greene, P. G. M. Wuts, Protective Groups in Organic Synthesis, John Wiley & Sons, Inc., New York, 1999). Suitable masks for the aldehyde function are e.g. olefins and thiazoles. The aldehyde may be converted to the cyano function using e.g. hydroxylamine in combination with e.g. formic acid, concentrated hydrochloric acid, polyphosphoric acid or pyridine-toluene. The intermediate oxime formed under these reaction conditions may be isolated before dehydration to deliver the final product. Alternative hydroxylamine reagents such as e.g. bistrifluoroacetylhydroxylamine and $NH_2OSO_3$ may be used as well and afford the nitrile without additional reagents. Further reagents applicable are e.g. $NH_4PO_4H_2$ and nitropropane in acetic acid, trimethylsilyl azide or S,S-dimethylsulfurdiimide.

Carboxamides may be suitable nitrile precursors, too. The conversion may be carried out with dehydrating agents such as e.g. trifluoroacetic acid anhydride, phosphorous pentoxide, $POCl_3$, $CCl_4$-phosphine combination, $Cl_3COCl$-amine combination, Burgess reagent, Vilsmeyer reagent, $SOCl_2$, or cyanuric chloride. Starting from the corresponding monoalkylated carboxamide, carboxylic acid, ester or carboxylic chloride the formation of the nitrile is also doable in one pot without the isolation of any intermediate.

Scheme 7: Introduction of the cyano residue from aniline precursor

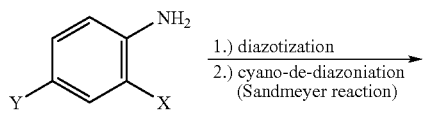

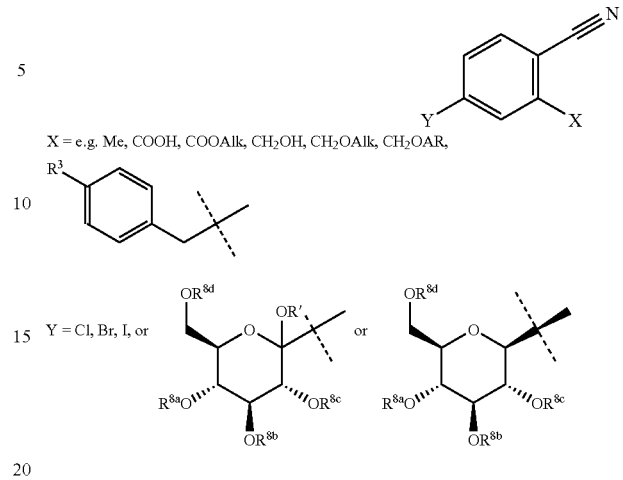

A well established approach to introduce the nitrile function is the so-called Sandmeyer reaction with copper cyanide and the corresponding diazonium compound accessible via diazotization of the respective aniline derivative. The synthesis of diazonium compounds and their subsequent cyano-de-diazoniation has extensively been documented in the organic chemistry literature.

Scheme 8: Alternative Synthesis of Diarylmethane Unit

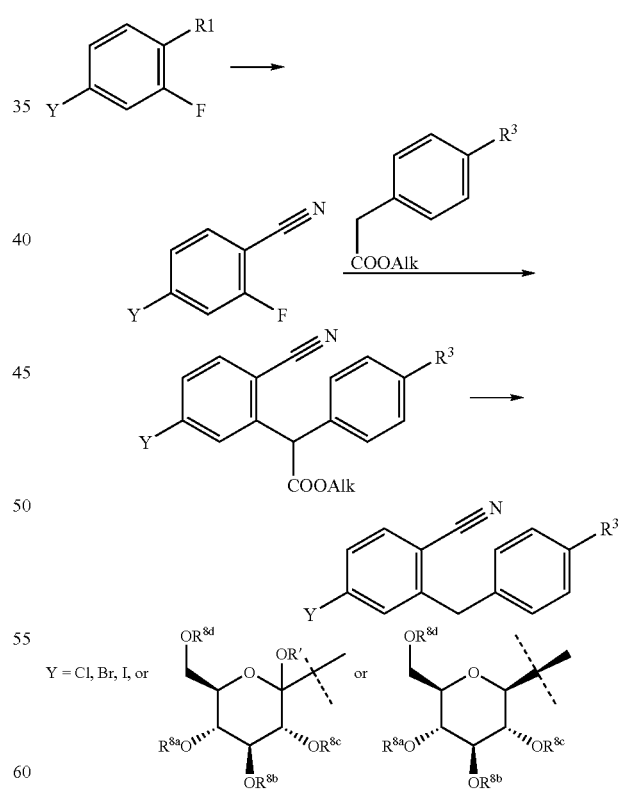

An alternative approach for the construction of the Diarylmethane Unit is shown in Scheme 8. It makes use of an ortho fluoro substituted benzonitrile which is either commercially available or can be obtained by methods mentioned before. The ortho fluoro substituted benzonitrile is reacted with an alkyl phenylacetate substituted by $R^3$ under basic conditions (see e.g. J. Org. Chem. 55, 1990, 4817-4821; J. Heterocycl. Chem., 32, 1995, 1461-1466) followed by ester cleavage and decarboxylation (see e.g. J. Heterocycl. Chem., 32, 1995, 1461-1466; Org. Prep. Proced. Int. 37, 2005, 550-555) or direct de-alkoxycarbonylation (see e.g. J. Med. Chem. 46, 2003, 5249-5257; Angew. Chem. Int. Ed. 47, 2004, 6493-6496).

In order to prepare compounds of general formula I, in process a) according to the invention, a compound of general formula II

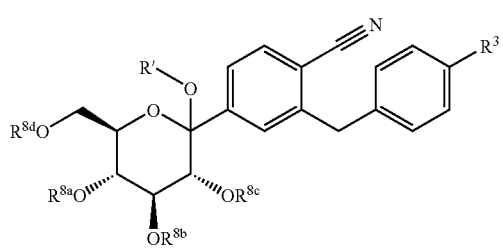

wherein R' and $R^3$ are as hereinbefore defined and
$R^{8a}$, $R^{8b}$, $R^{8c}$, $R^{8d}$ are as hereinbefore defined and independently of one another represent for example acetyl, pivaloyl, benzoyl, tert-butoxycarbonyl, benzyloxycarbonyl, allyl, trialkylsilyl, benzyl or substituted benzyl or in each case two adjacent groups $R^{8a}$, $R^{8b}$, $R^{8c}$, $R^{8d}$ form a benzylideneacetal or isopropylideneketal or a 2,3-dimethoxybutylene group which is linked via position 2 and 3 of the butylene group to the oxygen atoms of the pyranose ring and forms with them a substituted dioxane, which may be obtained as hereinbefore described, is reacted with a reducing agent in the presence of a Lewis or Brønsted acid.

Suitable reducing agents for the reaction include for example silanes, such as triethyl-, tripropyl-, triisopropyl- or diphenylsilane, sodium borohydride, sodium cyanoborohydride, zinc borohydride, boranes, lithium aluminium hydride, diisobutylaluminium hydride or samarium iodide. The reductions are carried out without or in the presence of a suitable Brønsted acid, such as e.g. hydrochloric acid, toluenesulphonic acid, trifluoroacetic acid or acetic acid, or Lewis acid, such as e.g. boron trifluoride etherate, trimethylsilyltriflate, titanium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. One particularly suitable combination of reagents consists for example of triethylsilane and boron trifluoride etherate, which is conveniently used in acetonitrile or dichloromethane at temperatures of −60° C. and 60° C. Moreover, hydrogen may be used in the presence of a transition metal catalyst, such as e.g. palladium on charcoal or Raney nickel, in solvents such as tetrahydrofuran, ethyl acetate, methanol, ethanol, water or acetic acid, for the transformation described.

Alternatively, in order to prepare compounds of general formula I according to process b) according to the invention, in a compound of general formula III

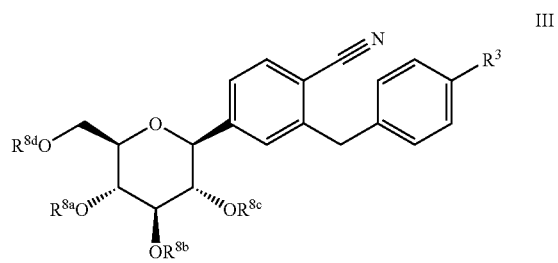

wherein $R^3$ is as hereinbefore defined and
$R^{8a}$ to $R^{8d}$ denote one of the protective groups defined hereinbefore, such as e.g. an acyl, arylmethyl, allyl, acetal, ketal or silyl group, and which may be obtained for example by reduction from the compound of formula II as hereinbefore described, the protective groups are cleaved.

It is understood that one or several of the groups $R^{8a}$, to $R^{8d}$ may be changed during the aforementioned synthetic processes.

Any acyl protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C. A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Any acetal or ketal protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or aprotically, e.g. in the presence of iodotrimethylsilane, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide.

In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

In the reactions described hereinbefore, any reactive groups present such as ethynyl, hydroxy, amino, alkylamino or imino groups may be protected during the reaction by conventional protecting groups which are cleaved again after the reaction.

For example, a protecting group for an ethynyl group may be the trimethylsilyl or triisopropyl group. The 2-hydroxyisoprop-2-yl group may also be used as a protective group.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds according to the invention are advantageously also obtainable using the methods described in the examples that follow, which may also be combined for this purpose with methods known to the skilled man from the literature, for example the methods described in WO 98/31697, WO 01/27128, WO 02/083066, WO 03/099836 and WO 2004/063209.

The present invention also relates to novel intermediate compounds as described in the reaction schemes hereinbefore and as described in the experimental section hereinafter.

In particular the following intermediate compounds are an additional aspect of the present invention:

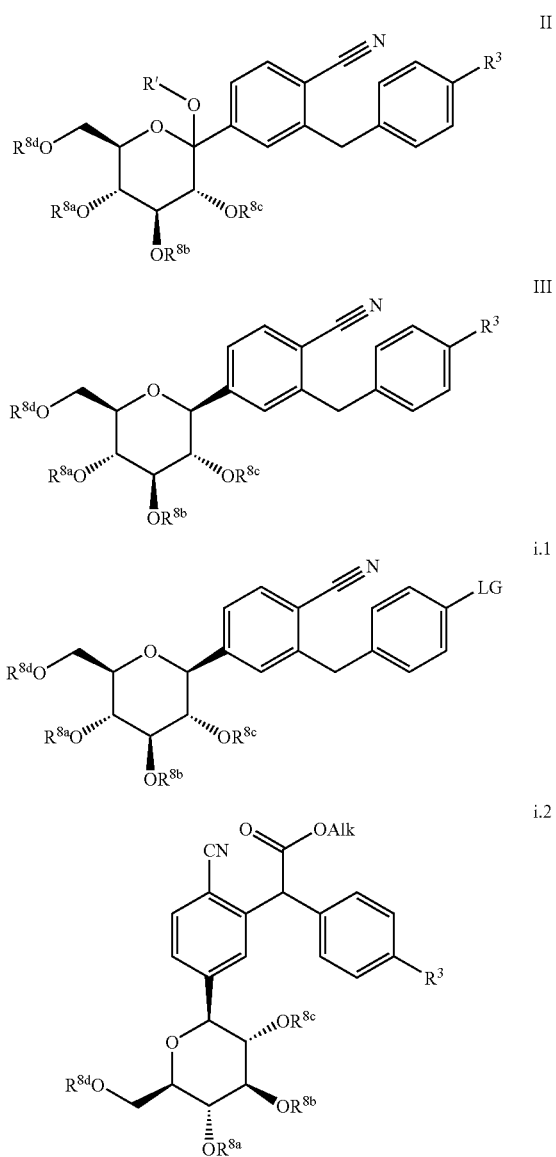

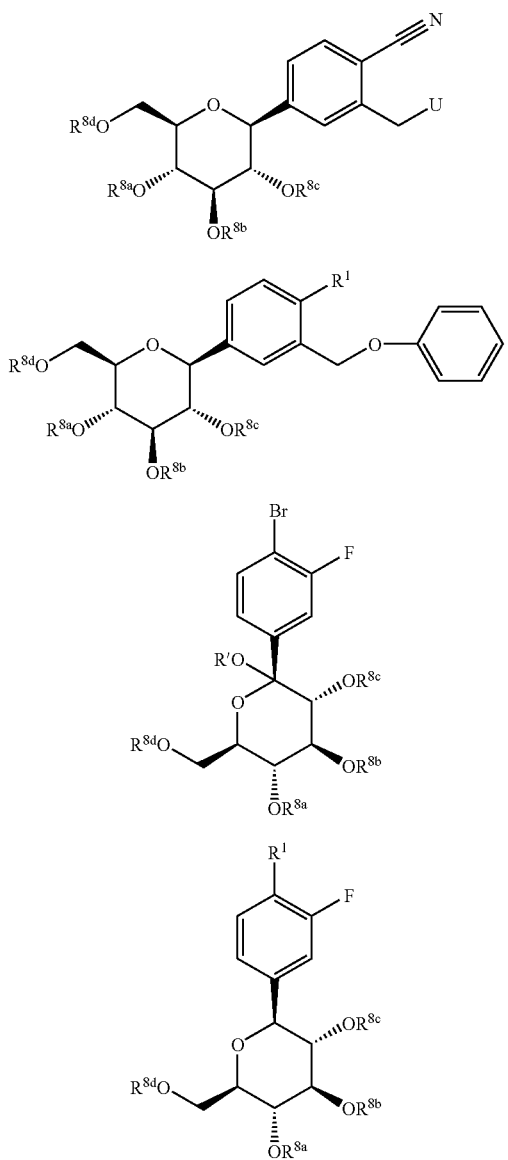

wherein
R$^{8a}$ to R$^{8d}$ are defined as hereinbefore and preferably denote H or acetyl;
R' is defined as hereinbefore and preferably denotes H, methyl or ethyl;
Alk denotes C$_{1-4}$-alkyl, preferably methyl or ethyl;
R$^1$ is defined as hereinbefore and preferably denotes Br or CN, most preferably CN;
R$^3$ is defined as hereinbefore, for example cyclopropyl or cyclobutyl, and is preferably selected from the group consisting of chloro, bromo, methyl, ethyl, n-propyl, i-propyl, cyclopropyl, cyclobutyl, cyclopentyl, hydroxy, cyano, (S)-tetrahydrofuran-3-yloxy, (R)-tetrahydrofuran-3-yloxy, C$_{3-7}$-cycloalkyl-oxy, C$_{1-3}$-alkyloxy, hydroxy;
LG denotes a leaving group such as Br, I, —O—(SO$_2$)—CF$_3$, preferably —O—(SO$_2$)—CF$_3$;
U denotes Cl, Br, I, —O—CO—C$_{1-4}$-alkyl, —O—C(=O)—O—C$_{1-4}$-alkyl or —OPO(O—C$_{1-4}$-alkyl)$_2$; preferably Br.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL-61) or alternatively a HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}$C-labelled alpha-methyl-glucopyranoside ($^{14}$C-AMG, Amersham) into the interior of the cell in a sodium-dependent manner.

The SGLT-2 assay is carried out as follows:

CHO-hSGLT2 cells are cultivated in Ham's F12 Medium (BioWhittaker) with 10% foetal calf serum and 250 µg/mL Zeocin (Invitrogen), and HEK293-hSGLT2 cells are cultivated in DMEM medium with 10% foetal calf serum and 250 µg/mL Zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. 40,000 cells per well are seeded into a white, 96-well plate coated with poly-D-lysine and incubated overnight at 37° C., 5% CO$_2$. The cells are washed twice with 250 µl of assay buffer (Hanks Balanced Salt Solution, 137 mM NaCl, 5.4 mM KCl, 2.8 mM CaCl$_2$, 1.2 mM MgSO$_4$ and 10 mM HEPES (pH 7.4), 50 µg/mL Gentamycin). 250 µl of assay buffer and 5 µl of test compound are then added to each well and the plate is incubated for further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% CO$_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM_000343) instead of hSGLT2 cDNA is expressed in CHO-K1 or HEK293 cells.

The compounds according to the invention may for example have EC50 values below 1000 nM, particularly below 200 nM, most preferably below 50 nM.

In view of their ability to inhibit the SGLT activity, the compounds according to the invention and the corresponding pharmaceutically acceptable salts thereof are suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

By the administration of a compound according to the invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a compound or a pharmaceutical composition according to the present invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, the compounds according to the invention, including the physiologically acceptable salts thereof, are suitable for the prevention or treatment of diabetes, particularly type 1 and type 2 diabetes mellitus, and/or diabetic complications.

In addition compounds according to the invention are particularly suitable for the prevention or treatment of overweight, obesity (including class I, class II and/or class III obesity), visceral obesity and/or abdominal obesity.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid 1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it. The terms "room temperature" and "ambient temperature" are used interchangeably and denote temperatures of about 20° C.

Preparation of the Starting Compounds:

EXAMPLE I

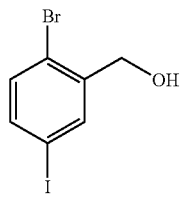

4-Bromo-3-hydroxymethyl-1-iodo-benzene

Oxalyl chloride (13.0 mL) is added to an ice-cold solution of 2-bromo-5-iodo-benzoic acid in CH$_2$Cl$_2$ (200 mL). DMF (0.2 mL) is added and the solution is stirred at room temperature for 6 h. Then, the solution is concentrated under reduced pressure and the residue is dissolved in THF (100 mL). The resulting solution is cooled in an ice-bath and LiBH$_4$ (3.4 g) is added in portions. The cooling bath is removed and the mixture is stirred at room temperature for 1 h. The reaction mixture is diluted with THF and treated with 0.1 M hydrochloric acid. Then, the organic layer is separated and the aqueous layer is extracted with ethyl acetate. The combined organic layers are dried (Na$_2$SO$_4$) and the solvent is evaporated under reduced pressure to give the crude product.

Yield: 47.0 g (99% of theory)

EXAMPLE II

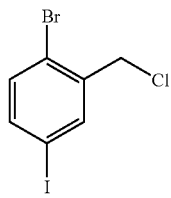

4-Bromo-3-chloromethyl-1-iodo-benzene

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 h. Then, the solvent and the excess reagent is removed under reduced pressure. The residue is triturated with methanol and dried.

Yield: 41.0 g (82% of theory)

EXAMPLE III

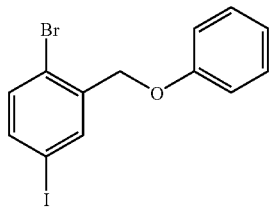

4-Bromo-1-iodo-3-phenoxymethyl-benzene

Phenol (13 g) dissolved in 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried and the solvent is evaporated under reduced pressure. The residue is purified by chromatography on silica gel (cyclohexane/ethyl acetate 19:1).

Yield: 38.0 g (79% of theory)

EXAMPLE IV

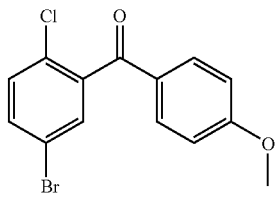

(5-Bromo-2-chloro-phenyl)-(4-methoxy-phenyl)-methanone 38.3 mL oxalyl chloride and 0.8 mL dimethylformamide are added to a mixture of 100 g 5-bromo-2-chloro-benzoic acid in 500 mL dichloromethane. The reaction mixture is stirred for 14 h, then filtered and separated from all volatile constituents in a rotary evaporator. The residue is dissolved in 150 mL dichloromethane, the resultant solution is cooled to −5° C., and 46.5 g anisole are added. Then 51.5 g aluminum trichloride are added batchwise so that the temperature does not exceed 5° C. The solution is stirred for 1 h at 1 to 5° C. and then poured onto crushed ice. The organic phase is separated off, and the aqueous phase is extracted with dichloromethane. The combined organic phases are washed with 1 M hydrochloric acid, twice with 1 M sodium hydroxide solution and with brine. Then the organic phase is dried over sodium sulfate, the solvent is removed and the residue is recrystallized from ethanol.

Yield: 86.3 g (64% of theory) Mass spectrum (ESI$^+$): m/z=325/327/329 (Br+Cl) [M+H]$^+$

EXAMPLE V

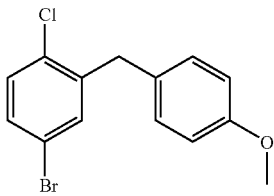

1-Bromo-4-chloro-3-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. Then with stirring 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h period at 45-50° C. and then cooled to ambient temperature. A solution of 28 g potassium hydroxide in 70 mL water is added and the resultant mixture is stirred for 2 h. The organic phase is separated and the aqueous phase is extracted another three times with diisopropylether. The combined organic phases are washed twice with 2 M potassium hydroxide solution and once with brine and then dried over sodium sulfate. After the solvent is evaporated, the residue is washed with ethanol and dried at 60° C.

Yield: 50.0 g (61% of theory) Mass spectrum (ESI$^+$): m/z=310/312/314 (Br+Cl) [M+H]$^+$

EXAMPLE VI

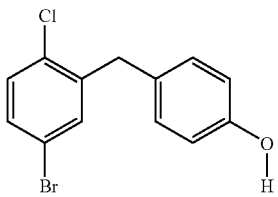

4-(5-bromo-2-chloro-benzyl)-phenol

A solution of 14.8 g 1-bromo-4-chloro-3-(4-methoxy-benzyl)-benzene in 150 mL dichloromethane is cooled in an ice bath. 50 mL of a 1 M solution of boron tribromide in dichloromethane are added and the resulting solution is stirred for 2 h at ambient temperature. The solution is then cooled in an ice bath again and saturated aqueous potassium carbonate solution is added dropwise. At ambient temperature the mixture is adjusted with aqueous 1 M hydrochloric acid to pH 1, the organic phase is separated off and the aqueous phase is extracted three times with ethyl acetate. The combined organic phases are dried over sodium sulfate and the solvent is removed completely.

Yield: 13.9 g (98% of theory) Mass spectrum (ESI$^-$): m/z=295/297/299 (Br+Cl) [M−H]$^-$

EXAMPLE VII

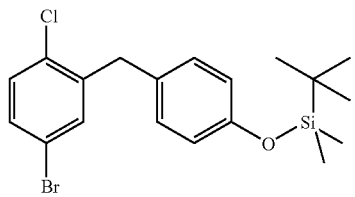

[4-(5-Bromo-2-chloro-benzyl)-phenoxy]-tert-butyl-dimethyl-silane

A solution of 13.9 g 4-(5-bromo-2-chloro-benzyl)-phenol in 140 mL dichloromethane is cooled in an ice bath. Then 7.54 g tert-butyldimethylsilyl chloride in 20 mL dichloromethane are added followed by 9.8 mL triethylamine and 0.5 g 4-dimethylaminopyridine. The resultant solution is stirred for 16 h at ambient temperature and then diluted with 100 mL dichloromethane. The organic phase is washed twice with aqueous 1 M hydrochloric acid and once with aqueous sodium hydrogen carbonate solution and then dried over sodium sulfate. After the solvent is removed, the residue is filtered through silica gel (cyclohexane/ethyl acetate 100:1).

Yield: 16.8 g (87% of theory) Mass spectrum (El): m/z=410/412/414 (Br+Cl) [M]$^+$

EXAMPLE VIII

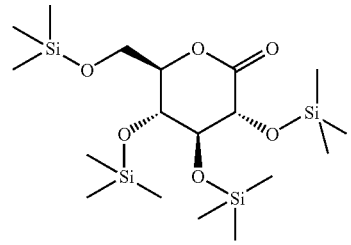

2,3,4,6-Tetrakis-O-(trimethylsilyl)-D-glucopyranone

A solution of 20 g D-glucono-1,5-lactone and 98.5 mL N-methylmorpholine in 200 mL of tetrahydrofuran is cooled to −5° C. Then 85 mL trimethylsilylchloride are added dropwise so that the temperature does not exceed 5° C. The solution is then stirred for 1 h at ambient temperature, 5 h at 35° C. and again for 14 h at ambient temperature. After the addition of 300 mL of toluene the solution is cooled in an ice bath and 500 mL of water are added so that the temperature does not exceed 10° C. The organic phase is separated and washed with aqueous sodium dihydrogen phosphate solution, water and brine. The solvent is removed and the residue is azeotropically dried with toluene.

Yield: 52.5 g (approx. 90% pure) Mass spectrum (ESI⁺): m/z=467 [M+H]⁺

EXAMPLE IX

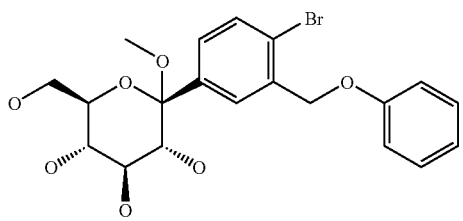

1-Bromo-4-(1-methoxy-D-glucopyranos-1-yl)-2-(phenoxymethyl)-benzene

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to −60° C. in argon atmosphere. The solution is warmed to −40° C. and then 2,3,4,6-tetrakis-O-(trimethylsilyl)-D-glucopyranone (10.7 g, 90% pure) in tetrahydrofuran (5 mL) is added. The resulting solution is warmed to −5° C. in the cooling bath and stirred for another 30 min at this temperature. Aqueous NH₄Cl solution is added and the resultant mixture is extracted with ethyl acetate. The combined organic extracts are dried over sodium sulphate and the solvent is removed under reduced pressure. The residue is dissolved in methanol (80 mL) and treated with methanesulfonic acid (0.6 mL). After stirring the reaction solution at 35-40° C. overnight, the solution is neutralized with solid NaHCO₃ and the methanol is removed under reduced pressure. The remainder is diluted with aqueous NaHCO₃ solution and the resulting mixture is extracted with ethyl acetate. The combined extracts are dried over sodium sulphate and the solvent is evaporated to yield the crude product that is submitted to reduction without further purification.

Yield: 7.8 g (93% of theory)

The following compounds may be obtained analogously to Example IX:

(1) 1-Bromo-4-(1-methoxy-D-glucopyranos-1-yl)-2-fluoro-benzene

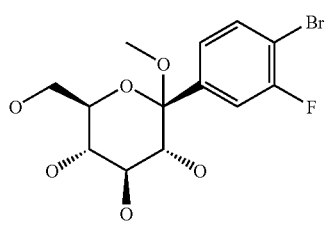

EXAMPLE X

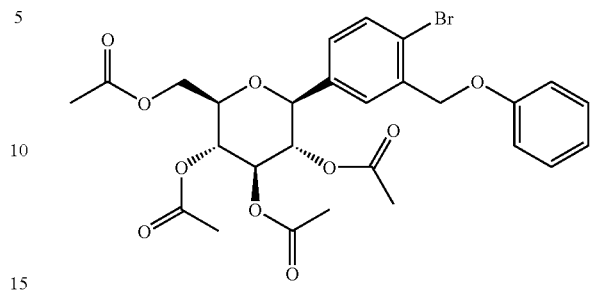

1-Bromo-4-(2,3,4,6-tetra-O-acetyl-D-glucopyranos-1-yl)-2-(phenoxymethyl)-benzene Boron trifluoride etherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to −20° C. at such a rate that the temperature maintains below −10° C. The resultant solution is warmed to 0° C. over a period of 1.5 h and then treated with aqueous sodium hydrogen carbonate solution. The resulting mixture is stirred for 0.5 h, the organic solvent is removed and the residue is extracted with ethyl acetate. The combined organic layers are dried over sodium sulphate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 h at ambient temperature and then diluted with dichloromethane. This solution is washed twice with 1 M hydrochloric acid and dried over sodium sulfate. After the solvent is removed, the residue is recrystallized from ethanol to furnish the product as a colorless solid.

Yield: 6.78 g (60% of theory) Mass spectrum (ESI⁺): m/z=610/612 (Br) [M+NH₄]⁺

The following compounds may be obtained analogously to Example X:

(1) 1-Bromo-4-(2,3,4,6-tetra-O-acetyl-D-glucopyranos-1-yl)-2-fluoro-benzene

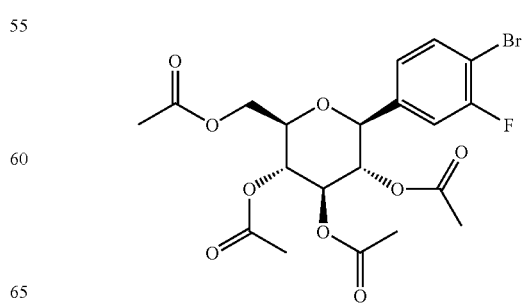

EXAMPLE XI

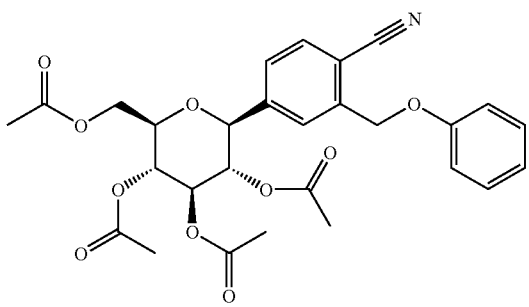

2-(Phenoxymethyl)-4-(2,3,4,6-tetra-O-acetyl-D-glucopyranos-1-yl)-benzonitrile

A flask charged with 1-bromo-4-(2,3,4,6-tetra-O-acetyl-D-glucopyranos-1-yl)-2-(phenoxymethyl)-benzene (5.4 g), zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then NMP (12 mL) is added and the resulting mixture is stirred at room temperature for 18 h. After dilution with ethyl acetate, the mixture is filtered and the filtrate is washed with aqueous sodium hydrogen carbonate solution. The organic phase is dried (sodium sulphate) and the solvent is removed. The residue is recrystallized from ethanol.

Yield: 4.10 g (84% of theory) Mass spectrum (ESI$^+$): m/z=557 [M+NH$_4$]$^+$

The following compounds may be obtained analogously to Example XI:

(1) 2-Fluoro-4-(2,3,4,6-tetra-O-acetyl-D-glucopyranos-1-yl)-benzonitrile

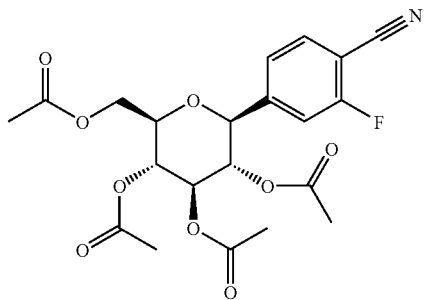

EXAMPLE XII

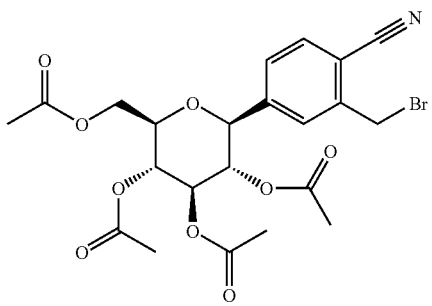

2-Bromomethyl-4-(2,3,4,6-tetra-O-acetyl-D-glucopyranos-1-yl)-benzonitrile

A 33% solution of hydrobromic acid in acetic acid (15 mL) is added to a solution of 2-phenyloxymethyl-4-(2,3,4,6-tetra-O-acetyl-D-glucopyranos-1-yl)-benzonitrile (0.71 g) and acetic anhydride (0.12 mL) in acetic acid (10 ml). The resulting solution is stirred at 55° C. for 6 h and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl aceate/cyclohexane (1:5), and the precipitate is separated by filtration and dried at 50° C. to give the pure product.

Yield: 0.52 g (75% of theory) Mass spectrum (ESI$^+$): m/z=543/545 (Br) [M+NH$_4$]$^+$

EXAMPLE XIII

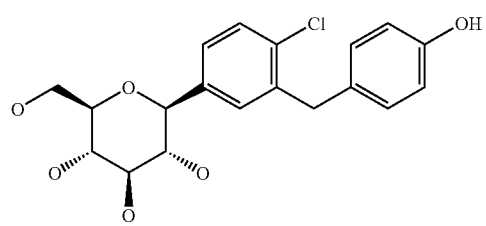

1-Chloro-4-(β-D-glucopyranos-1-yl)-2-(4-hydroxybenzyl)-benzene

A solution of 4.0 g [4-(5-Bromo-2-chloro-benzyl)-phenoxy]-tert-butyl-dimethyl-silane in 42 mL dry diethyl ether is cooled to −80° C. under argon. 11.6 mL of a chilled (ca. −50° C.) 1.7 M solution of tert-butyllithium in pentane are slowly added to the cooled solution and then the solution is stirred for 30 min at −80° C. This solution is then added dropwise through a transfer needle, which is cooled with dry ice, to a solution of 4.78 g 2,3,4,6-tetrakis-O-(trimethylsilyl)-D-glucopyranone in 38 mL diethyl ether chilled to −80° C. The resulting solution is stirred for 3 h at −78° C. Then a solution of 1.1 mL methanesulfonic acid in 35 mL methanol is added and the resultant reaction solution is stirred for another 16 h at ambient temperature. The solution is then neutralized with solid sodium hydrogen carbonate, ethyl acetate is added and the resultant solution is concentrated under reduced pressure. Aqueous sodium hydrogen carbonate solution is added to the remaining solution that is extracted four times with ethyl acetate. The combined organic phases are dried over sodium sulfate and the solvent is evaporated. The residue is dissolved in 30 mL acetonitrile and 30 mL dichloromethane and the resulting solution is cooled to −10° C. After the addition of 4.4 mL triethylsilane, 2.6 mL boron trifluoride etherate are added dropwise so that the temperature does not exceed −5° C. After the addition is complete, the reaction solution is stirred for another 5 h at −5 to −10° C. and then quenched by the addition of aqueous sodium hydrogen carbonate solution. The organic phase is separated and the aqueous phase is extracted four times with ethyl acetate. The combined organic phases are dried over sodium sulfate, the solvent is removed and the residue is purified by chromatography on silica gel (dichloromethane/methanol). The product then obtained is an approx. 6:1 mixture of β/αwhich can be separated by global acetylation of the hydroxyl groups with acetic anhydride, pyridine and 4-dimethylaminopyridine in dichloromethane and recrystallisation of the resulting acetylated product from ethanol. The pure acetylated β-product thus obtained is converted into the title compound by removal of the acetyl groups in methanol with 4 M potassium hydroxide solution.

Yield: 1.6 g (46% of theory) Mass spectrum (ESI⁺): m/z=398/400 (Cl) [M+NH₄]⁺

EXAMPLE XIV

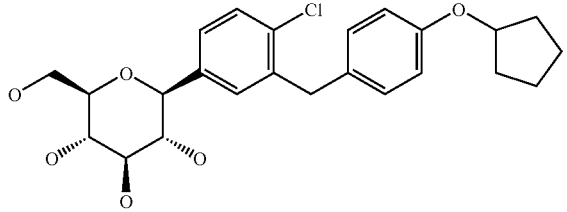

1-Chloro-2-(4-cyclopentyloxybenzyl)-4-(β-D-glucopyranos-1-yl)-benzene 0.16 mL Iodocyclopentane are added to a mixture of 0.25 g 1-chloro-4-(β-D-glucopyranos-1-yl)-2-(4-hydroxybenzyl)-benzene and 0.4 g caesium carbonate in 2.5 mL of dimethylformamide. The mixture is stirred for 4 h at 45° C., before another 0.1 g caesium carbonate and 0.05 ml iodocyclopentane are added. After another 14 h stirring at 45° C. aqueous sodium chloride solution is added and the resulting mixture is extracted with ethyl acetate. The organic phase is dried over sodium sulfate, the solvent is removed and the residue is purified using silica gel (dichloromethane/methanol 1:0->5:1).

Yield: 0.23 g (78% of theory) Mass spectrum (ESI⁺): m/z=466/468 (Cl) [M+NH₄]⁺

The following compounds are obtained analogously to Example XIV:

(1) 1-Chloro-4-(β-D-glucopyranos-1-yl)-2-[4-((R)-tetrahydrofuran-3-yloxy)-benzyl]-benzene The reaction is carried out with tetrahydrofuran-3-yl (S)-toluene-4-sulfonate as the coupling partner.

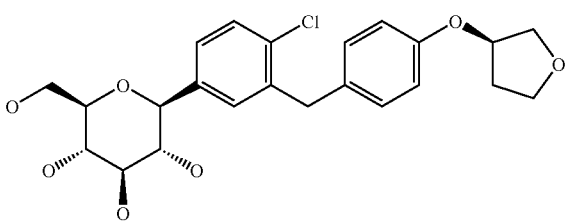

Mass spectrum (ESI⁺): m/z=451/453 (Cl) [M+H]⁺

(2) 1-Chloro-4-(β-D-glucopyranos-1-yl)-2-[4-((S)-tetrahydrofuran-3-yloxy)-benzyl]-benzene The reaction is carried out with tetrahydrofuran-3-yl (R)-toluene-4-sulfonate as the coupling partner.

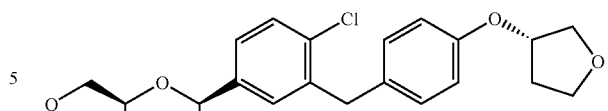

Mass spectrum (ESI⁺): m/z=451/453 (Cl) [M+H]⁺

(3) 1-Chloro-2-(4-cyclobutyloxy-benzyl)-4-(β-D-glucopyranos-1-yl)-benzene

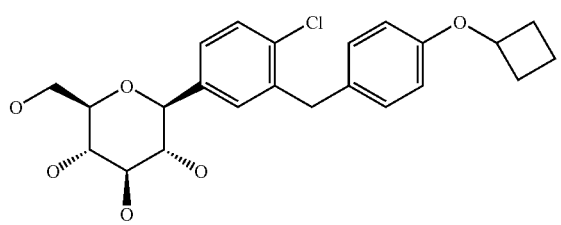

Mass spectrum (ESI⁺): m/z=452/454 (Cl) [M+NH₄]⁺

(4) 1-Chloro-2-(4-cyclohexyloxy-benzyl)-4-(β-D-glucopyranos-1-yl)-benzene

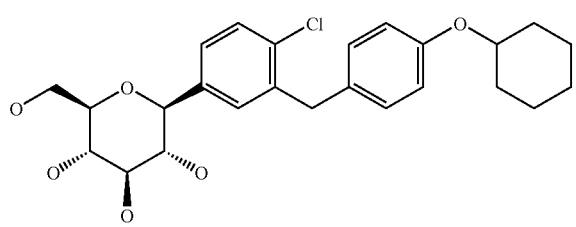

Mass spectrum (ESI⁺): m/z=480/482 (Cl) [M+NH₄]⁺

(5) 1-Chloro-4-(β-D-glucopyranos-1-yl)-2-[4-(tetrahydropyran-4-yloxy)-benzyl]-benzene

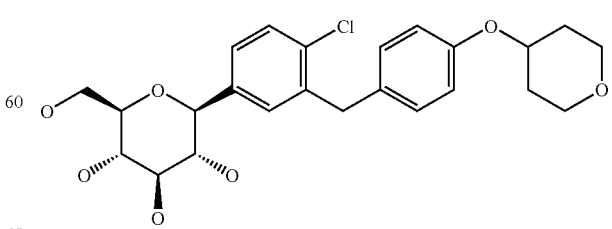

Mass spectrum (ESI⁺): m/z=487/489 (Cl) [M+Na]⁺

(6) 2-[4-(1-Acetyl-piperidin-4-yloxy)-benzyl]-1-chloro-4-(β-D-glucopyranos-1-yl)-benzene The reaction is carried out with 1-acetyl-4-methylsulfonyloxy-piperidine as the electrophile.

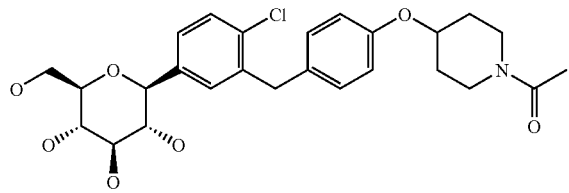

Mass spectrum (ESI⁺): m/z=506/508 (Cl) [M+H]⁺

(7) 1-Chloro-4-(β-D-glucopyranos-1-yl)-2-(4-methoxy-benzyl)-benzene

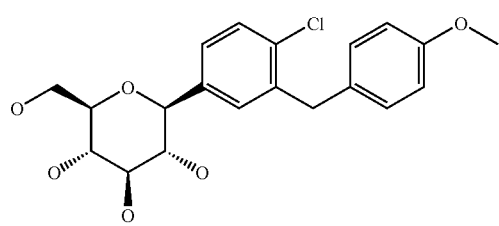

Mass spectrum (ESI⁺): m/z=412/414 (Cl) [M+NH₄]⁺

(8) 1-Chloro-2-(4-ethoxy-benzyl)-4-(β-D-glucopyranos-1-yl)-benzene

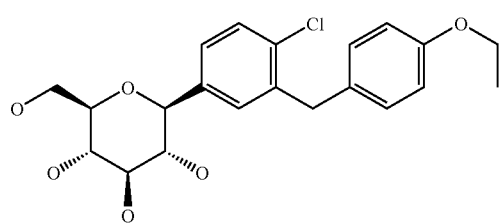

Mass spectrum (ESI⁺): m/z=426/428 (Cl) [M+NH₄]⁺

(9) 1-Chloro-4-(β-D-glucopyranos-1-yl)-2-(4-isopropoxy-benzyl)-benzene

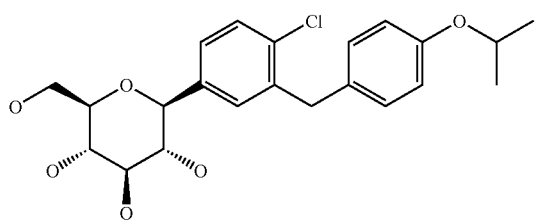

EXAMPLE XV

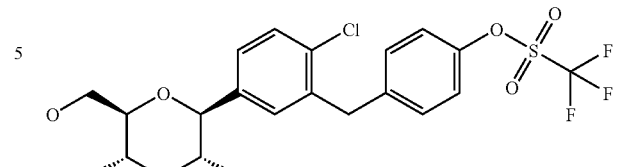

1-Chloro-4-(β-D-glucopyranos-1-yl)-2-[4-(trifluoromethylsulfonyloxy)-benzyl]-benzene 10 mg 4-dimethylaminopyridine are added to a solution of 0.38 g 1-chloro-4-(β-D-glucopyranos-1-yl)-2-(4-hydroxy-benzyl)-benzene, 0.21 ml triethylamine and 0.39 g N,N-bis-(trifluoromethanesulfonyl)-aniline in 10 ml dry dichloromethane. The solution is stirred for 4 h at ambient temperature and then combined with brine. The resulting mixture is extracted with ethyl acetate, the organic extracts are dried over sodium sulfate, and the solvent is removed. The residue is purified by chromatography on silica gel (dichloromethane/methanol 1:0->4:1).

Yield: 0.33 g (64% of theory) Mass spectrum (ESI⁺): m/z=530/532 (Cl) [M+NH₄]⁺

The following compounds are obtained analogously to Example XV:

(1) 1-Cyano-4-(β-D-glucopyranos-1-yl)-2-[4-(trifluoromethylsulfonyloxy)-benzyl]-benzene

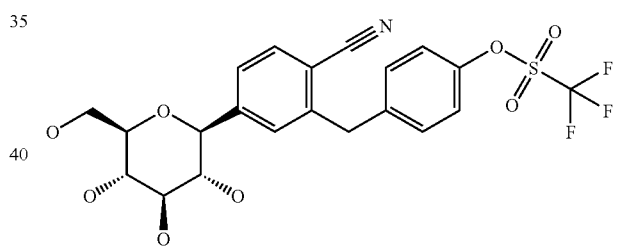

Mass spectrum (ESI⁺): m/z=504 [M+H]+

EXAMPLE XVI

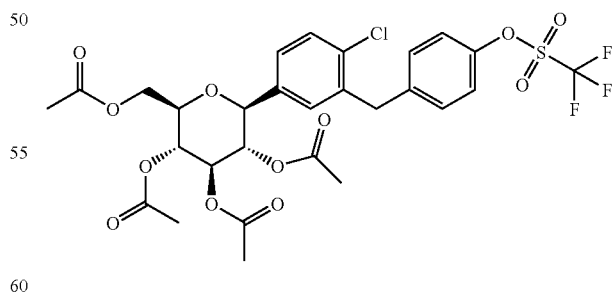

1-Chloro-4-(2,3,4,6-tetra-O-acetyl-β-D-glucopyranos-1-yl)-2-[4-(trifluoromethylsulfonyloxy)-benzyl]-benzene To a solution of 5.6 g 1-chloro-4-(β-D-glucopyranos-1-yl)-2-[4-(trifluoromethylsulfonyloxy)-benzyl]-benzene in mL dichloromethane is added consecutively 7 mL pyridine, 7.8 mL acetic anhydride and 0.12 g 4-dimethylaminopyridine. The solution is stirred at ambient temperature for 1 h. After adding 50 mL of water, the resultant mixture is stirred for another 5 min. The organic phase is separated and washed with aqueous 1 M hydrochloric acid and aqueous sodium hydrogen carbonate solution. After drying over magnesium sulfate and evaporation of the organic solvent, the product is yielded as white solid.

Yield: 7.0 g (94% of theory) Mass spectrum (ESI$^+$): m/z=698/700 (Cl) [M+NH$_4$]$^+$ The following compounds are obtained analogously to Example XVI:

(1) 1-Cyano-4-(2,3,4,6-tetra-O-acetyl-β-D-glucopyranos-1-yl)-2-[4-(trifluoromethylsulfonyloxy)-benzyl]-benzene

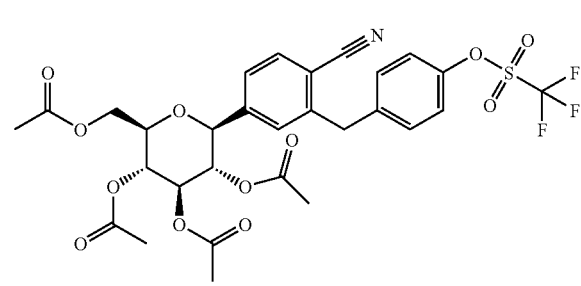

Mass spectrum (ESI$^+$): m/z=689 [M+NH$_4$]$^+$

EXAMPLE XVII

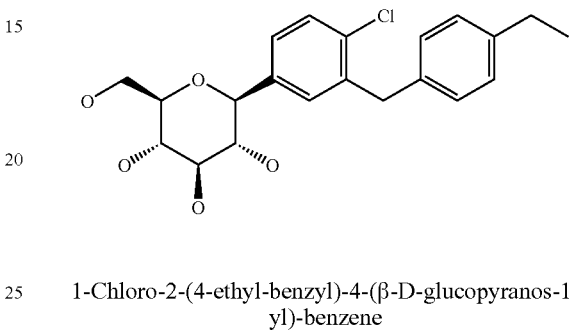

1-Chloro-2-(4-ethynyl-benzyl)-4-(β-D-glucopyranos-1-yl)-benzene 25 mg of copper iodide, 44 mg of bis-(triphenylphosphine)-palladium dichloride, 0.30 ml triethylamine and finally 0.14 ml of trimethylsilylacetylene are added under argon to a solution of 0.32 g 1-chloro-4-(β-D-glucopyranos-1-yl)-2-[4-(trifluoromethylsulphonyloxy)-benzyl]-benzene in 3 ml of dimethylformamide. The flask is tightly sealed and the mixture is stirred for 8 h at 90° C. Then another 25 mg of bis-(triphenylphosphine)-palladium dichloride and 0.1 ml trimethylsilylacetylene are added, and the solution is stirred for a further 10 h at 90° C. Then aqueous sodium hydrogen carbonate solution is added, the resultant mixture is extracted three times with ethyl acetate, and the combined organic phases are dried over sodium sulfate. After the solvent has been evaporated, the residue is dissolved in 5 ml of methanol and combined with 0.12 g potassium carbonate. The mixture is stirred for 1 h at ambient temperature and then neutralised with 1 M hydrochloric acid. Then the methanol is evaporated off, the residue is combined with brine and extracted with ethyl acetate. The organic extracts collected are dried over sodium sulfate, and the solvent is removed. The residue is purified by chromatography on silica gel (dichloromethane/methanol 1:0->5:1).

Yield: 0.095 g (40% of theory) Mass spectrum (ESI$^+$): m/z=406/408 (Cl) [M+NH$_4$]$^+$

EXAMPLE XVIII

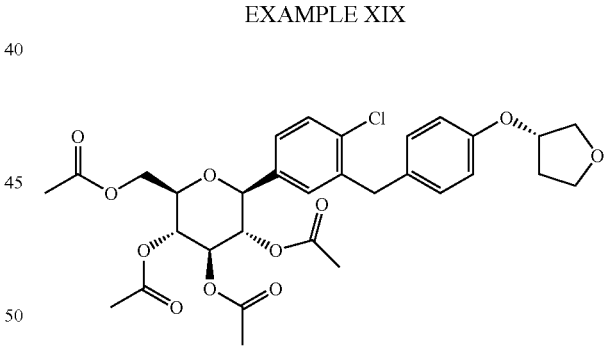

1-Chloro-2-(4-ethyl-benzyl)-4-(β-D-glucopyranos-1-yl)-benzene 2.87 g 1-chloro-2-(4-ethynyl-benzyl)-4-(β-D-glucopyranos-1-yl)-benzene are dissolved in 10 ml of ethyl acetate and 5 ml of ethanol. 0.3 g 10% palladium on carbon are added and the resultant mixture is stirred under hydrogen atmosphere (1 atm) overnight. The reaction mixture is filtered over Celite and the filtrate is concentrated. The residue is purified by chromatography on silica gel (dichloromethane/methanol 1:0->5:1).

Yield: 1,0 g (34% of theory) Mass spectrum (ESI$^+$): m/z=410/412 (Cl) [M+NH$_4$]$^+$

EXAMPLE XIX

1-Chloro-2-[4-((S)-tetrahydrofuran-3-yloxy)-benzyl]-4-(2,3,4,6-tetra-O-acetyl-β-D-glucopyranos-1-yl)-benzene To a solution of 2.02 g 1-chloro-4-(β-D-glucopyranos-1-yl)-2-[4-((S)-tetrahydrofuran-3-yloxy)-benzyl]-benzene in 20 mL dichloromethane is added in succession 2.5 mL pyridine, 2.8 mL acetic anhydride and 50 mg 4-dimethylaminopyridine. The reaction solution is stirred at ambient temperature for 4 h. The solution is diluted with 50 mL dichloromethane, washed twice with 50 mL 1 M hydrochloric acid and once with sodium hydrogencarbonate solution. After drying over sodium sulfate, the solvent is evaporated to yield the product.

Yield: 2.53 g (91% of theory) Mass spectrum (ESI⁺): m/z=642/644 (Cl) [M+Na]+

The following compounds may be obtained analogously to Example XIX:

(1) 1-Chloro-2-[4-((R)-tetrahydrofuran-3-yloxy)-benzyl]-4-(2,3,4,6-tetra-O-acetyl-β-D-glucopyranos-1-yl)-benzene

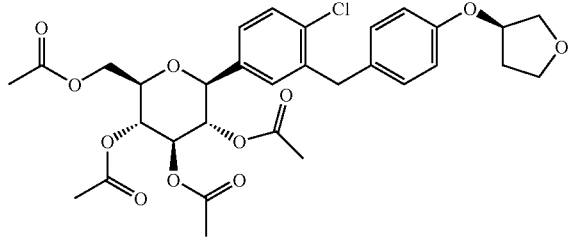

(2) 1-Chloro-2-(4-cyclopentyloxy-benzyl)-4-(2,3,4,6-tetra-O-acetyl-β-D-glucopyranos-1-yl)-benzene

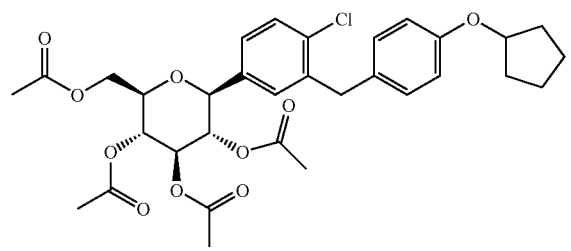

Mass spectrum (ESI⁺): m/z=634/636 (Cl) [M+NH₄]⁺

(3) 1-Chloro-2-(4-cyclobutyloxy-benzyl)-4-(2,3,4,6-tetra-O-acetyl-β-D-glucopyranos-1-yl)-benzene

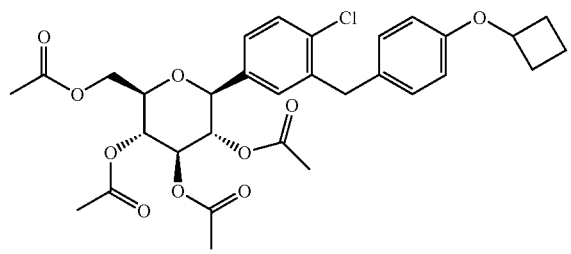

(4) 1-Chloro-2-(4-cyclohexyloxy-benzyl)-4-(2,3,4,6-tetra-O-acetyl-β-D-glucopyranos-1-yl)-benzene

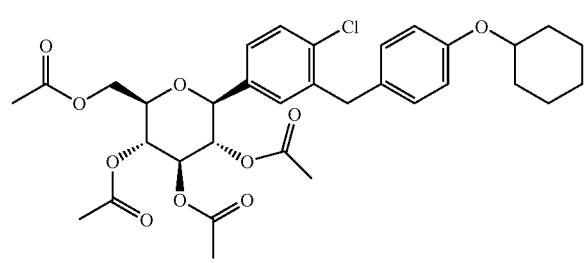

(5) 1-Chloro-4-(2,3,4,6-tetra-O-acetyl-β-D-glucopyranos-1-yl)-2-[4-(tetrahydropyran-4-yloxy)-benzyl]-benzene

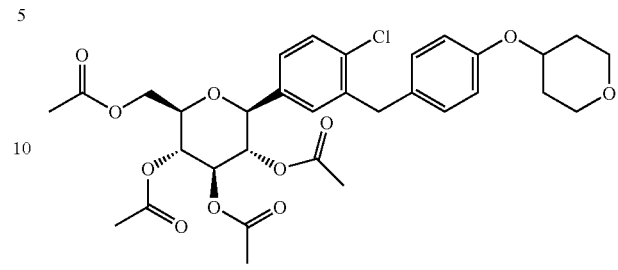

(6) 2-[4-(1-Acetyl-piperidin-4-yloxy)-benzyl]-1-chloro-4-(2,3,4,6-tetra-O-acetyl-β-D-glucopyranos-1-yl)-benzene

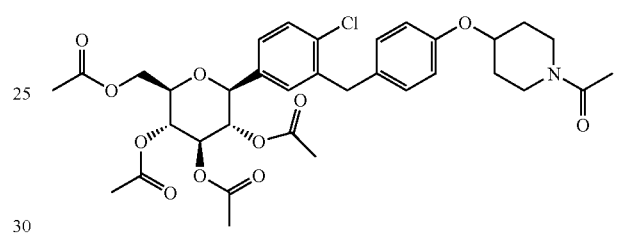

(7) 1-Chloro-2-(4-methoxy-benzyl)-4-(2,3,4,6-tetra-O-acetyl-β-D-glucopyranos-1-yl)-benzene

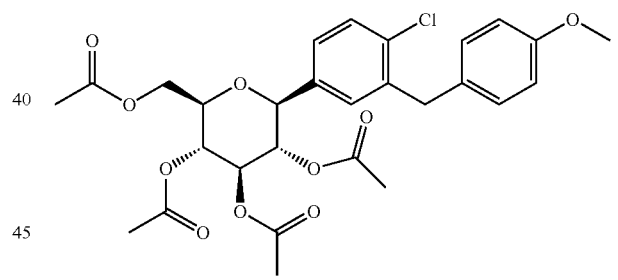

Mass spectrum (ESI⁺): m/z=585/587 (Cl) [M+NH₄]⁺

(8) 1-Chloro-2-(4-ethoxy-benzyl)-4-(2,3,4,6-tetra-O-acetyl-β-D-glucopyranos-1-yl)-benzene

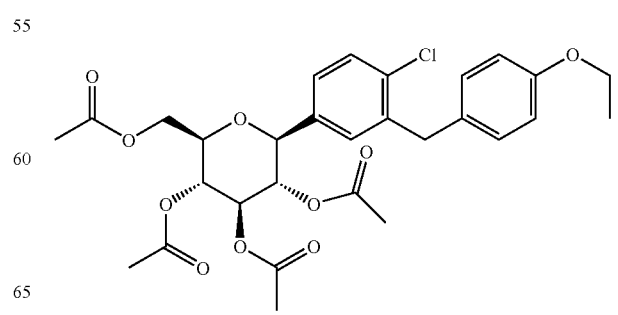

(9) 1-Chloro-2-(4-isopropoxy-benzyl)-4-(2,3,4,6-tetra-O-acetyl-β-D-glucopyranos-1-yl)-benzene

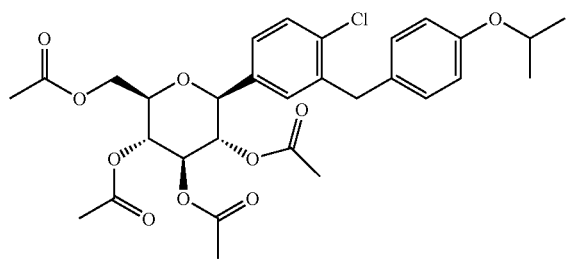

(10) 1-Chloro-2-(4-ethyl-benzyl)-4-(2,3,4,6-tetra-O-acetyl-β-D-glucopyranos-1-yl)-benzene

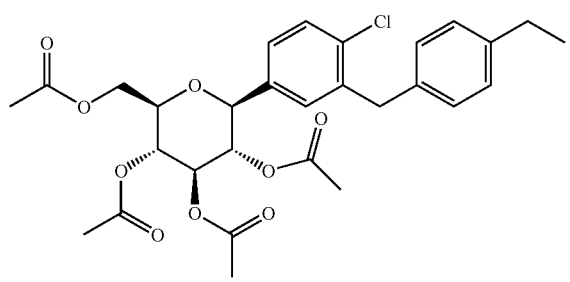

(11) 2-(4-Acetoxy-benzyl)-1-chloro-4-(2,3,4,6-tetra-O-acetyl-β-D-glucopyranos-1-yl)-benzene

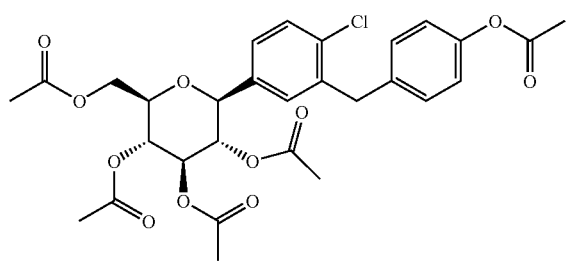

Mass spectrum (ESI⁺): m/z=608/610 (Cl) [M+NH₄]⁺

EXAMPLE XX

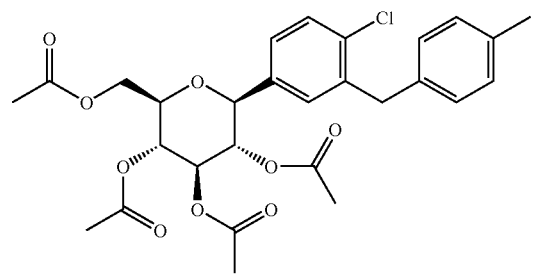

1-Chloro-2-(4-methyl-benzyl)-4-(2,3,4,6-tetra-O-acetyl-β-D-glucopyranos-1-yl)-benzene Diisobutylaluminumhydride (54 μL, 1 mol/l in toluene) is added to a mixture of 1,1'-bis(diphenylphosphino)ferrocene-dichloropalladium(II) (22 mg) in THF (3 mL) in Ar atmosphere and chilled in an ice-bath. The mixture is stirred in the ice-bath for 0.5 h and then 1-chloro-4-(2,3,4,6-tetra-O-acetyl-β-D-glucopyranos-1-yl)-2-[4-(trifluoromethylsulfonyloxy)-benzyl]-benzene (0.60 g) and Me₂Zn (0.88 mL, 1 mol/L in toluene) are added in succession. The ice-bath is removed and the mixture is heated at reflux for 2.5 h. After cooling to room temperature, 1 M hydrochloric acid is added and the resulting mixture is extracted with ethyl acetate. The extracts collected are dried over sodium sulfate, and the solvent is removed. The residue is purified by chromatography on silica gel (cyclohexane/ethyl acetate 1:0->2:1).

Yield: 0.25 g (52% of theory)

EXAMPLE XXI

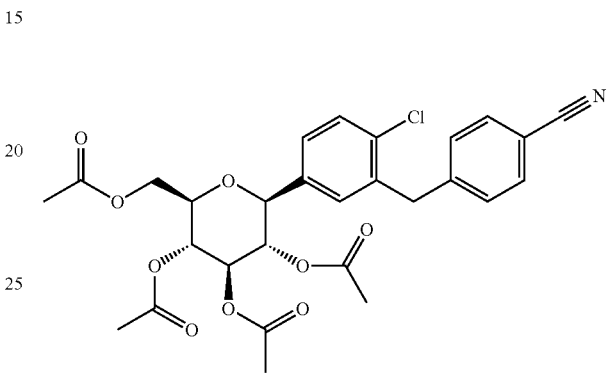

1-Chloro-2-(4-cyano-benzyl)-4-(2,3,4,6-tetra-O-acetyl-β-D-glucopyranos-1-yl)-benzene Tetrakis(triphenylphosphine)palladium(0) (0.13 g) is added to a flask charged with 1-chloro-4-(2,3,4,6-tetra-O-acetyl-β-D-glucopyranos-1-yl)-2-[4-(trifluoromethylsulfonyloxy)-benzyl]-benzene (0.80 g) and zinc cyanide (0.14 g) in Ar atmosphere. The mixture is stirred at 100° C. for 3 h. After cooling to room temperature, ethyl acetate is added and the resulting mixture is filtered, washed with aqueous NaHCO₃ solution, dried (sodium sulphate) and the solvent is removed. The residue is recrystallized from ethanol.

Yield: 0.45 g (69% of theory) Mass spectrum (ESI⁺): m/z=580/582 (Cl) [M+Na]⁺

EXAMPLE XXII

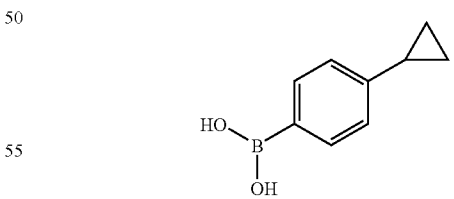

4-Cyclopropyl-phenylboronic acid 2.5 M nButyllithium in hexane (14.5 mL) is added dropwise to 1-bromo-4-cyclopropyl-benzene (5.92 g) in THF (14 mL) and toluene (50 mL) chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated. The aqueous phase is extracted with ethyl acetate and the combined organic phases are dried (sodium sulphate). The solvent is evaporated and the residue is washed with a mixture of ether and cyclohexane to give the product as a colorless solid.

Yield: 2.92 g (60% of theory) Mass spectrum (ESI⁻): m/z=207 (Cl) [M+HCOO]⁻

The following compounds may be obtained analogously to Example XXII:

(1) 4-Difluoromethoxy-phenylboronic acid

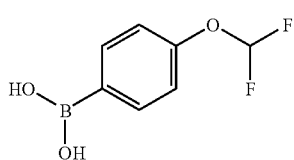

Mass spectrum (ESI⁻): m/z=233 (Cl) [M+HCOO]⁻

In a departure from the procedure described above the compound is prepared from 4-difluoromethoxy-1-iodo-benzene using iPrMgCl to generate the arylmetal compound and trapping this intermediate with trimethyl borate.

(2) 4-Difluoromethyl-phenylboronic acid

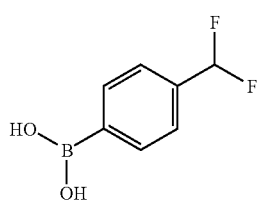

Mass spectrum (ESI⁺): m/z=172 (Cl) [M+H]⁺

In a departure from the procedure described above the compound is prepared from 4-difluoromethyl-1-iodo-benzene (prepared from 4-iodobenzaldehyde using diethylaminosulfurtrifluoride (DAST) in dichloromethane) using iPrMgCl to generate the arylmetal compound and trapping this intermediate with trimethyl borate.

EXAMPLE XXIII

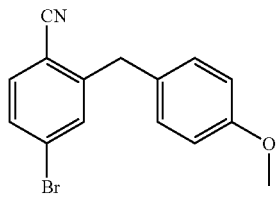

1-Bromo-4-cyano-3-(4-methoxy-benzyl)-benzene

A mixture of 25 g of ethyl (4-methoxy-phenyl)-acetate, 27.4 g of 1-bromo-4-cyano-3-fluoro-benzene and 20 mL of N-methyl-pyrrolidin-2-one is slowly added to 31.4 g of potassium tert butoxide in 130 mL of N-methyl-pyrrolidin-2-one keeping the temperature below 10° C. After stirring for 1 hour at room temperature, 100 mL of methanol and 137 mL of 1 M aqueous sodium hydroxide are added and the mixture is stirred overnight at room temperature. The methanol fraction is evaporated, the residue is basified with 1 M aqueous sodium hydroxide and extracted with tert butyl-methyl ether. The aqueous phase is acidified with 4 M hydrochloric acid and extracted with ethyl acetate several times. The combined ethyl acetate extracts are evaporated and the residue together with 120 mL of N,N-dimethyl formamide and 24.9 g of potassium carbonate heated at 100° C. for 1 hour. The reaction mixture is diluted with aqueous sodium bicarbonate and extracted several times with ethyl acetate. The combined extracts are evaporated and the residue crystallized from methanol.

Yield: 13 g (33% of theory) Mass spectrum (ESI⁺): m/z=319/321 (Br) [M+NH₄]⁺

EXAMPLE XXIV

Ethyl 4-cyclopropyl-phenylacetate

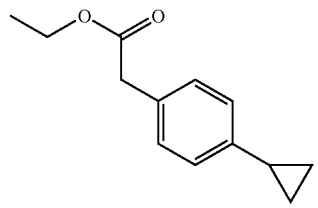

Prepared from Ethyl 4-bromo-phenylacetate by transition metal catalyzed coupling with cyclopropylboronic acid using tricyclohexylphosphonium tetrafluoroborate, palladium acetate, potassium phosphate in toluene and water according to *Tetrahedron Lett.* 2002, 43, 6987-6990

Mass spectrum (ESI⁺): m/z=205 [M+H]⁺

Preparation of the End Compounds:

EXAMPLE 1

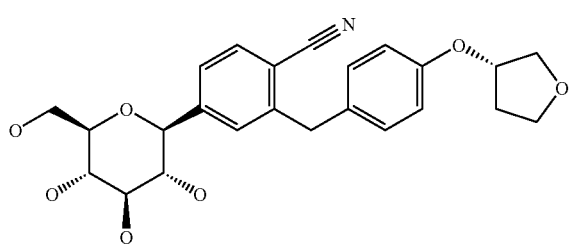

4-(β-D-glucopyranos-1-yl)-2-[4-((S)-tetrahydrofuranyl-3-oxy)-benzyl]-benzonitrile A mixture of 1.00 g 1-chloro-2-[4-((S)-tetrahydrofuranyl-3-oxy)-benzyl]-4-(2,3,4,6-tetra-O-acetyl-β-D-glucopyranos-1-yl)-benzene, 0.16 sodium cyanide and 0.35 g nickel bromide in 2.5 mL N-methyl-2-pyrrolidinone is heated in a microwave oven at 220° C. for 15 min. After cooling to room temperature, water is added and the resultant mixture is extracted with ethyl acetate. After drying over sodium sulfate and evaporation of the solvent, the residue is dissolved in 5 mL methanol. 4 mL of 4 M aqueous potassium hydroxide solution is added and the reaction solution is stirred at ambient temperature for 3 h. The solution is neutralized with 1 M hydrochloric acid and the methanol is evaporated. The residue is extracted with ethylacetate, the combined extracts are dried over sodium sulfate and the solvent is removed under reduced pressure. The residue is purified by chromatography on silica gel (dichloromethane/methanol 4:1).

Yield: 0.35 g (49% of theory) Mass spectrum (ESI⁺): m/z=442 [M+H]⁺

The following compounds may be obtained analogously to Example 1:

(2) 4-(β-D-glucopyranos-1-yl)-2-[4-((R)-tetrahydrofuran-3-yloxy)-benzyl]-benzonitrile

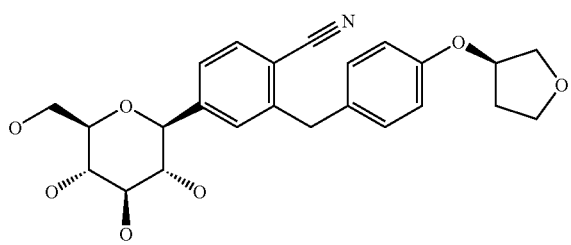

(3) 2-(4-Cyclopentyloxy-benzyl)-4-(β-D-glucopyranos-1-yl)-benzonitrile

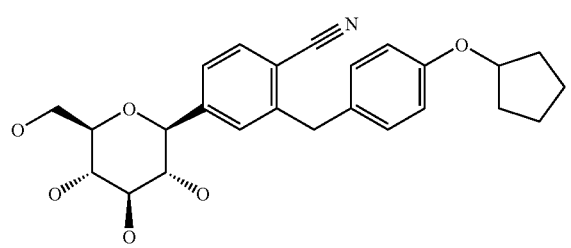

(4) 2-(4-Cyclobutyloxy-benzyl)-4-(β-D-glucopyranos-1-yl)-benzonitrile

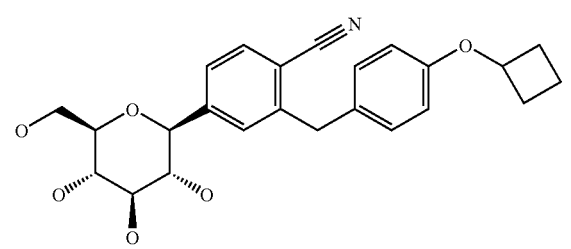

(5) 2-(4-Cyclohexyloxy-benzyl)-4-(β-D-glucopyranos-1-yl)-benzonitrile

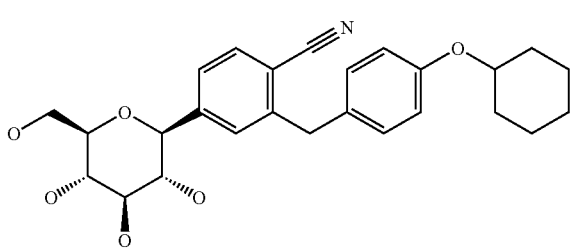

(6) 2-[4-(Tetrahydropyran-4-yloxy)-benzyl]-4-(β-D-glucopyranos-1-yl)-benzonitrile

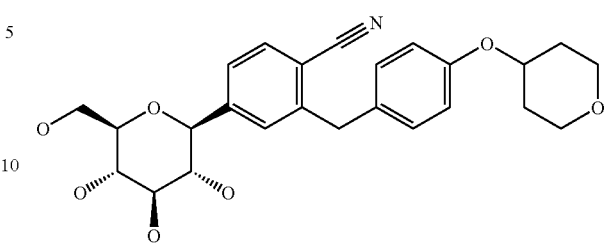

(7) 2-[4-(1-Acetyl-piperidin-4-yloxy)-benzyl]-4-(β-D-glucopyranos-1-yl)-benzonitrile

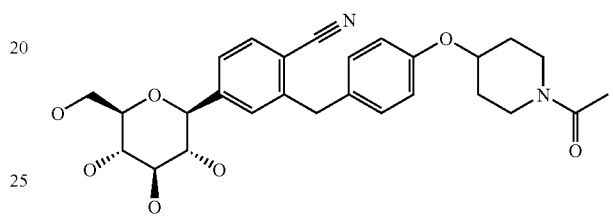

(8) 2-(4-Methoxy-benzyl)-4-(β-D-glucopyranos-1-yl)-benzonitrile

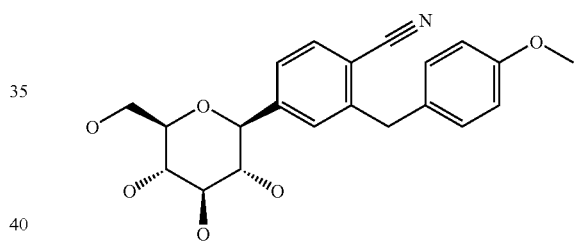

Mass spectrum (ESI⁺): m/z=403 [M+NH₄]⁺

This compound is also obtained from 1-bromo-4-cyano-3-(4-methoxybenzyl)-benzene (Example XXIII) and 2,3,4,6-tetrakis-O-(trimethylsilyl)-D-glucopyranone in a manner analogous to Example XIII except that the reaction with tert-butyllithium is done in tetrahydrofuran at −87° C. and that the reaction with methanol/methanesulfonic acid is performed at 55° C.

(9) 2-(4-Ethoxy-benzyl)-4-(β-D-glucopyranos-1-yl)-benzonitrile

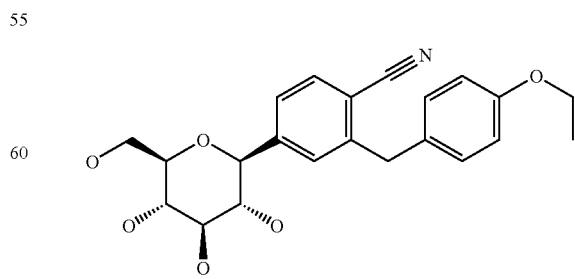

Mass spectrum (ESI⁺): m/z=417 [M+NH₄]⁺

(10) 4-(β-D-glucopyranos-1-yl)-2-(4-isopropoxy-benzyl)-benzonitrile

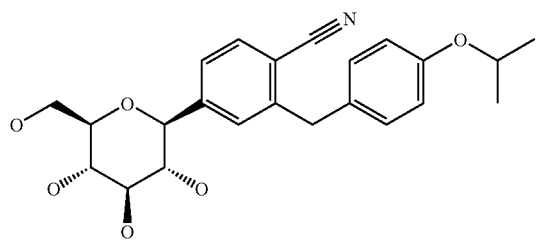

Mass spectrum (ESI⁺): m/z=431 [M+NH$_4$]$^+$

(11) 2-(4-Ethyl-benzyl)-4-(β-D-glucopyranos-1-yl)-benzonitrile

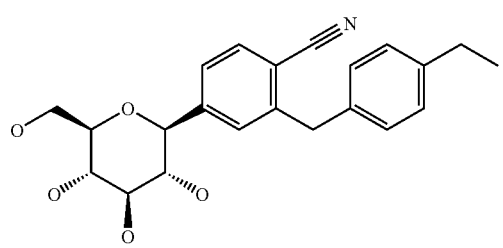

Mass spectrum (ESI⁺): m/z=401 [M+NH$_4$]$^+$

(12) 4-(β-D-glucopyranos-1-yl)-2-(4-hydroxy-benzyl)-benzonitrile

The compound was prepared from 2-(4-acetoxy-benzyl)-1-chloro-4-(2,3,4,6-tetra-O-acetyl-β-D-glucopyranos-1-yl)-benzene

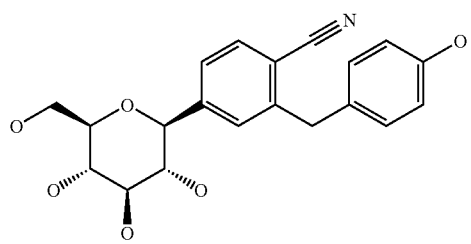

Mass spectrum (ESI⁺): m/z=389 [M+NH$_4$]$^+$

The compound is also obtained by peracetylation of 2-(4-Methoxy-benzyl)-4-(β-D-glucopyranos-1-yl)-benzonitrile (Compound 1(8)) followed by ether cleavage with boron tribromide and deacetylation.

(13) 4-(β-D-glucopyranos-1-yl)-2-(4-methyl-benzyl)-benzonitrile

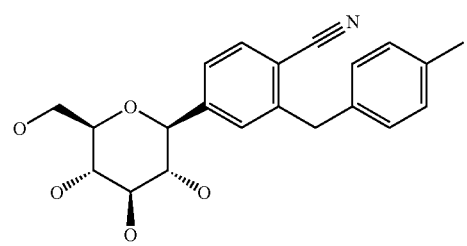

Mass spectrum (ESI⁺): m/z=387 [M+NH$_4$]$^+$

(14) 2-(4-Cyano-benzyl)-4-(β-D-glucopyranos-1-yl)-benzonitrile

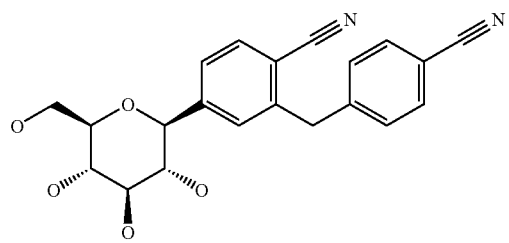

Mass spectrum (ESI⁺): m/z=398 [M+NH$_4$]$^+$

EXAMPLE 15

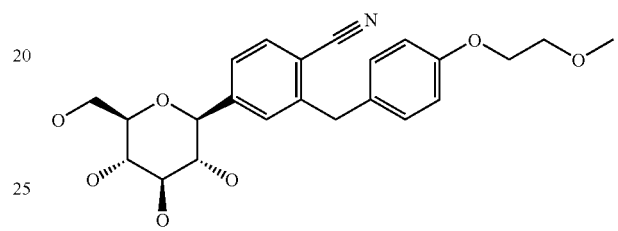

4-(β-D-glucopyranos-1-yl)-2-(4-methoxyethoxy-benzyl)-benzonitrile

2-Bromoethyl methyl ether (85 μl) is added to a mixture of 4-(β-D-glucopyranos-1-yl)-2-(4-hydroxybenzyl)-benzonitrile (0.30 g) and cesium carbonate (0.39 g) in 3 mL of dimethylformamide. The mixture is stirred at 80° C. for 16 h, before water and brine are added. The resulting mixture is extracted with ethyl acetate, the combined extracts are dried over sodium sulphate and the solvent is removed under reduced pressure. The residue is purified by chromatography on silica gel (dichloromethane/methanol 1:0->5:1).

Yield: 0.19 g (49% of theory) Mass spectrum (ESI⁺): m/z=430 [M+H]$^+$

EXAMPLE 16

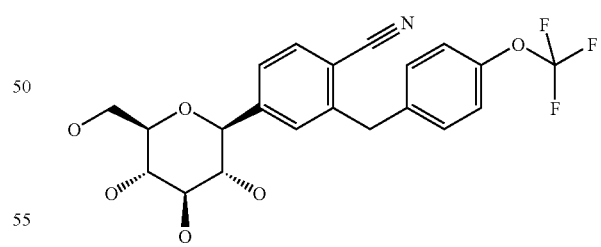

4-(β-D-glucopyranos-1-yl)-2-(4-trifluoromethoxy-benzyl)-benzonitrile

An Ar filled flask is charged with 2-bromomethyl-4-(2,3,4,6-tetra-O-acetyl-D-glucopyranos-1-yl)-benzonitrile (0.25 g), 4-trifluoromethoxy-phenylboronic acid (0.20 g), potassium carbonate (0.26 g) and a 3:1 mixture of degassed acetone and water (4 mL). The mixture is stirred at room temperature for 5 min, before it is cooled in an ice-bath. Then palladium dichloride (5 mg) is added and the reaction mixture is stirred for 16 h at ambient temperature. The mixture is then diluted with brine and extracted with ethyl acetate. The combined extracts are dried over sodium sulfate and the solvent is removed under reduced pressure. The residue is dissolved in methanol (9 mL) and treated with 4 M aqueous potassium hydroxide solution (1 mL). The resulting solution is stirred at ambient temperature for 1 h and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0->8:1).

Yield: 0.145 g (69% of theory) Mass spectrum (ESI$^+$): m/z=457 [M+NH$_4$]$^+$

The following compounds may be obtained analogously to Example 16:

(17) 4-(β-D-glucopyranos-1-yl)-2-(4-trifluoromethyl-benzyl)-benzonitrile

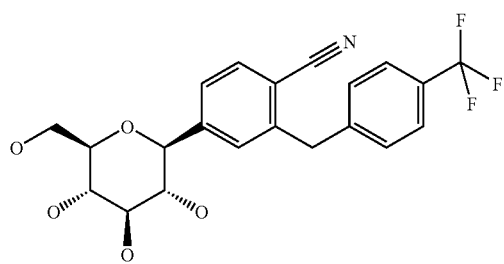

Mass spectrum (ESI$^+$): m/z=441 [M+NH$_4$]$^+$

(18) 4-(β-D-glucopyranos-1-yl)-2-(4-isopropyl-benzyl)-benzonitrile

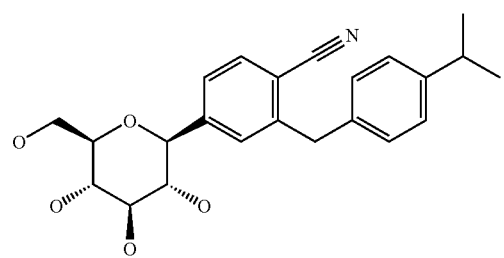

Mass spectrum (ESI$^+$): m/z=415 [M+NH$_4$]$^+$

(19) 4-(β-D-glucopyranos-1-yl)-2-(4-tert-butyl-benzyl)-benzonitrile

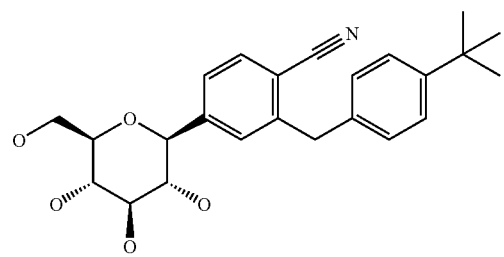

Mass spectrum (ESI$^+$): m/z=429 [M+NH$_4$]$^+$

(20) 4-(β-D-glucopyranos-1-yl)-2-(4-trimethylsilyl-benzyl)-benzonitrile

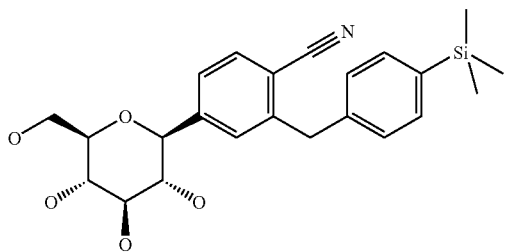

Mass spectrum (ESI$^+$): m/z=445 [M+NH$_4$]$^+$

(21) 4-(β-D-glucopyranos-1-yl)-2-(4-methylsulfanyl-benzyl)-benzonitrile

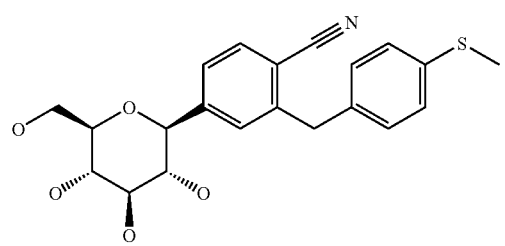

Mass spectrum (ESI$^+$): m/z=419 [M+NH$_4$]$^+$

(22) 4-(β-D-glucopyranos-1-yl)-2-[4-(3-methyl-but-1-yl)-benzyl]-benzonitrile

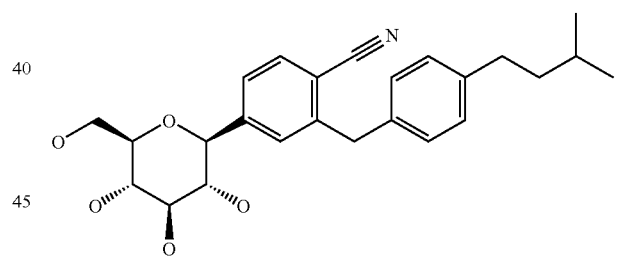

Mass spectrum (ESI$^+$): m/z=443 [M+NH$_4$]$^+$

(23) 2-(4-Fluoro-benzyl)-4-(β-D-glucopyranos-1-yl)-benzonitrile

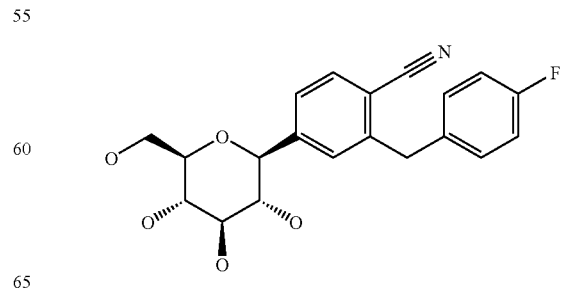

Mass spectrum (ESI$^+$): m/z=391 [M+NH$_4$]$^+$

(24) 2-(4-Chloro-benzyl)-4-(β-D-glucopyranos-1-yl)-benzonitrile

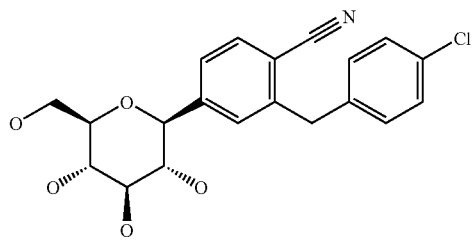

Mass spectrum (ESI⁺): m/z=407/409 (Cl) [M+NH$_4$]⁺

(25) 2-(4-Difluoromethoxy-benzyl)-4-(β-D-glucopyranos-1-yl)-benzonitrile

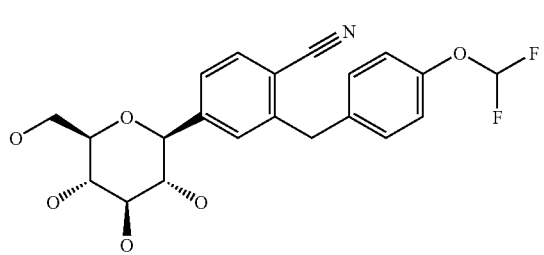

Mass spectrum (ESI⁺): m/z=439 [M+NH$_4$]⁺

(26) 2-(4-Difluoromethyl-benzyl)-4-(β-D-glucopyranos-1-yl)-benzonitrile

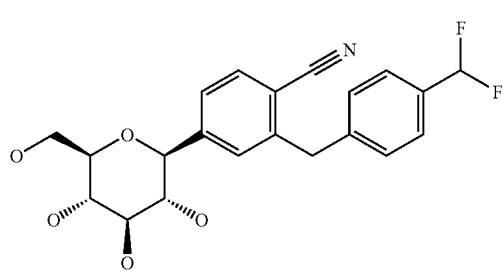

Mass spectrum (ESI⁺): m/z=423 [M+NH$_4$]⁺

(27-1) 2-(4-Cyclopropyl-benzyl)-4-(β-D-glucopyranos-1-yl)-benzonitrile

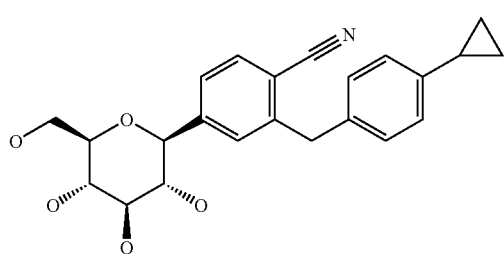

Mass spectrum (ESI⁺): m/z=413 [M+NH$_4$]⁺

The compound is obtained according to example 16 wherein instead of 4-trifluoromethoxy-phenylboronic acid the educt (XXII) 4-cyclopropyl-phenylboronic acid is taken.

The compound (27) is also obtained by transition metal catalyzed coupling of either 2-(4-bromo-benzyl)-4-(2,3,4,6-tetra-O-acetyl-β-D-glucopyranos-1-yl)-benzonitrile or 1-cyano-4-(2,3,4,6-tetra-O-acetyl-β-D-glucopyranos-1-yl)-2-[4-(trifluoromethylsulfonyloxy)-benzyl]-benzene (Compound XVI(1)) with cyclopropylboronic acid using tricyclohexylphosphonium tetrafluoroborate, palladium acetate, potassium phosphate in toluene and water according to *Tetrahedron Lett.* 2002, 43, 6987-6990 and followed by deacetylation of the coupling product with KOH in methanol.

Compound (27) may also be obtained by reacting 2-Fluoro-4-(2,3,4,6-tetra-O-acetyl-D-glucopyranos-1-yl)-benzonitrile (Compound XI(1)) and Ethyl 4-cyclopropyl-phenylacetate (Compound XXIV) under basic conditions followed by ester hydrolysis and decarboxylation.

(27-2) 2-(4-Cyclobutyl-benzyl)-4-(β-D-glucopyranos-1-yl)-benzonitrile

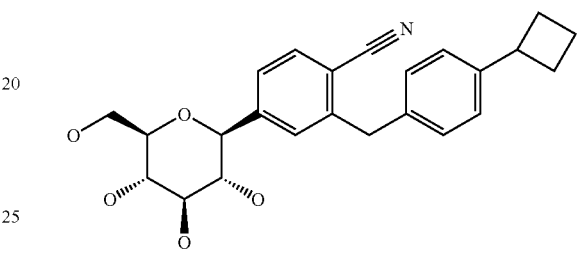

The compound is obtained according to example (27-1) wherein for example instead of 4-cyclopropylboronic acid 4-cyclobutylboronic acid (obtainable in analogy to example XXII) is taken.

Mass spectrum (ESI⁺): m/z=427 [M+NH$_4$]⁺

(28) 4-(β-D-glucopyranos-1-yl)-2-(4-prop-1-yl-benzyl)-benzonitrile

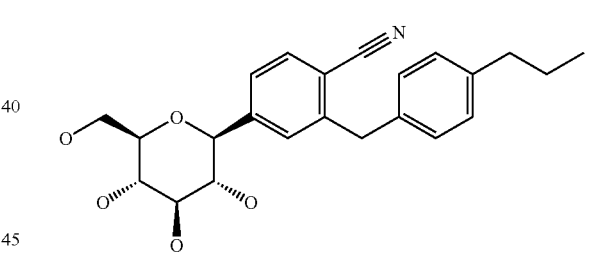

Mass spectrum (ESI⁺): m/z=415 [M+NH$_4$]⁺

EXAMPLE 29

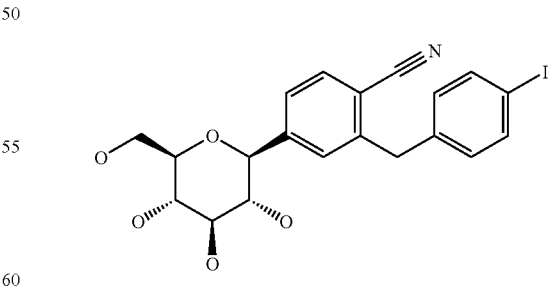

4-(β-D-glucopyranos-1-yl)-2-(4-iodo-benzyl)-benzonitrile

A 1 M solution of iodine monochloride in dichloromethane (0.9 mL) is added to 4-(β-D-glucopyranos-1-yl)-2-(4-trimethylsilyl-benzyl)-benzonitrile (0.26 g) dissolved in dichloromethane (5 mL). The solution is stirred at room temperature for 1 h and then quenched by the addition of aqueous Na$_2$S$_2$O$_3$ solution and aqueous NaHCO$_3$ solution. The organic phase is separated and the aqueous phase is extracted with ethyl acetate. The combined organic phases are dried over sodium sulfate and the solvent is removed. The residue is chromatographed on silica gel (dichloromethane/methanol 1:0->8:1).

Yield: 0.15 g (88% of theory) Mass spectrum (ESI$^+$): m/z=499 [M+NH$_4$]$^+$

The following compounds may be obtained analogously to Example 29:

(30) 2-(4-Bromo-benzyl)-4-(β-D-glucopyranos-1-yl)-benzonitrile

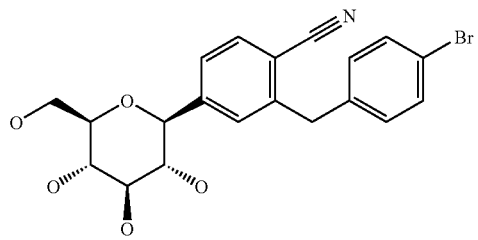

Mass spectrum (ESI$^+$): m/z=451/453 [M+NH$_4$]$^+$

The compound is obtained according to the procedure of Example 29 using bromine in dichloromethane.

EXAMPLE 31

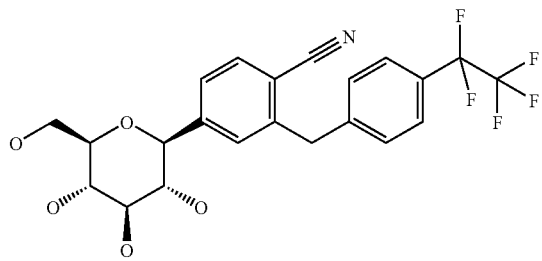

4-(β-D-glucopyranos-1-yl)-2-(4-pentafluoroethyl-benzyl)-benzonitrile

A flask charged with 4-(2,3,4,6-tetra-O-acetyl-β-D-glucopyranos-1-yl)-2-(4-iodo-benzyl)-benzonitrile (0.16 g), pentafluoroethyltrimethylsilane (0.14 g), KF (43 mg), CuI (0.16 g), DMF (2 mL) and Ar atmosphere is heated at 60° C. for 24 h. Then, aqueous NaHCO$_3$ solution is added and the resulting mixture is extracted with ethyl acetate. The combined organic phases are dried over sodium sulfate and the solvent is removed. The residue is dissolved in methanol (8 mL) and treated with 4 M KOH solution (0.8 mL). The solution is stirred at room temperature for 1 h and then diluted with aqueous NaHCO$_3$ solution. After removal of the methanol under reduced pressure, the residue is extracted with ethyl acetate, the combined organic extracts are dried and the solvent is removed. The residue is chromatographed on silica gel (dichloromethane/methanol 1:0->8:1).

Yield: 0.08 g (69% of theory) Mass spectrum (ESI$^+$): m/z=491 [M+NH$_4$]$^+$

EXAMPLE 32

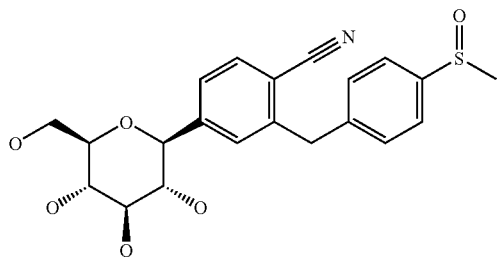

4-(β-D-glucopyranos-1-yl)-2-(4-methylsulfinyl-benzyl)-benzonitrile

35% Hydrogen peroxide in water (48 μL) is added to 4-(β-D-glucopyranos-1-yl)-2-(4-methylsulfanyl-benzyl)-benzonitrile (83 mg) in 1,1,1,3,3,3-hexafluoroisopropanol (2 mL). The resulting solution is stirred at ambient temperature for 1 h and then quenched by the addition of aqueous Na$_2$S$_2$O$_3$ solution and aqueous NaHCO$_3$ solution. The organic phase is separated and the aqueous phase is extracted with ethyl acetate. The combined organic phases are dried over sodium sulfate and the solvent is removed. The residue is chromatographed on silica gel (dichloromethane/methanol 1:0->5:1).

Yield: 24 mg (28% of theory) Mass spectrum (ESI$^+$): m/z=418 [M+H]$^+$

EXAMPLE 33

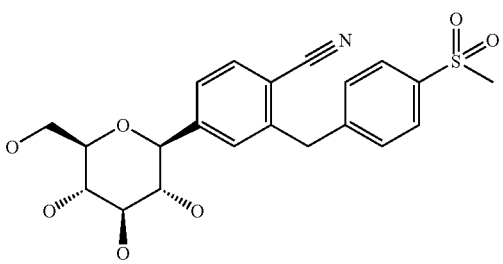

4-(β-D-glucopyranos-1-yl)-2-(4-methylsulfonyl-benzyl)-benzonitrile

3-Chloroperoxybenzoic acid (70%, 0.14 g) is added to 4-(β-D-glucopyranos-1-yl)-2-(4-methylsulfanyl-benzyl)-benzonitrile (100 mg) in dichloromethane (2 mL) chilled in an ice-bath. The cooling bath is removed and the resulting solution is stirred at ambient temperature for 1 h. After the addition of aqueous Na$_2$S$_2$O$_3$ solution and aqueous NaHCO$_3$ solution, the organic phase is separated and the aqueous phase is extracted with ethyl acetate. The combined organic phases are dried over sodium sulfate and the solvent is removed. The residue is chromatographed on silica gel (dichloromethane/methanol 1:0->8:1).

Yield: 68 mg (63% of theory) Mass spectrum (ESI$^+$): m/z=451 [M+NH$_4$]$^+$

The following compounds may also be prepared analogously to the above-mentioned Examples or other methods known from the literature:

| Ex. | Structure |
|---|---|
| 34 | 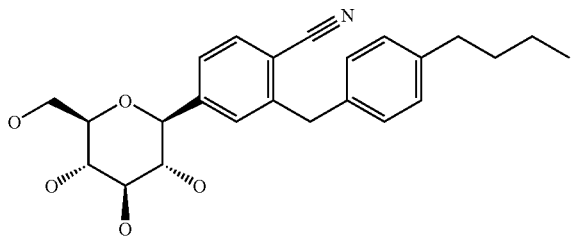 |
| 35 | 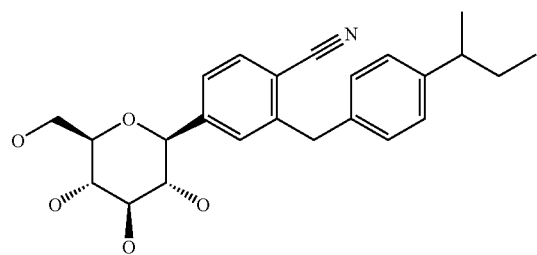 |
| 36 | 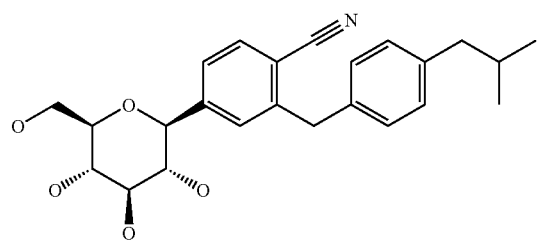 |
| 37 | 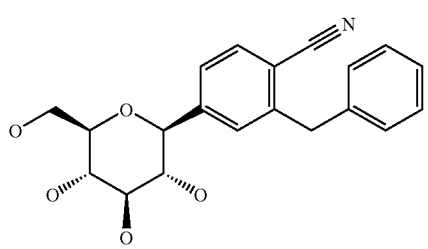 |
| 38 | 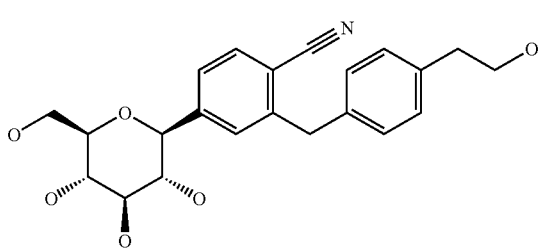 |

| Ex. | Structure |
|---|---|
| 39 | 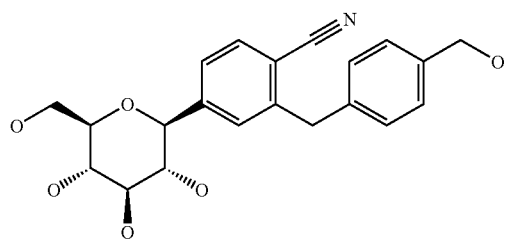 |
| 40 | 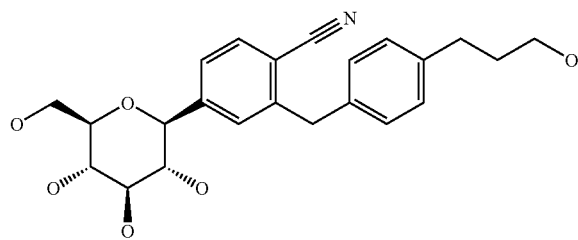 |
| 41 | 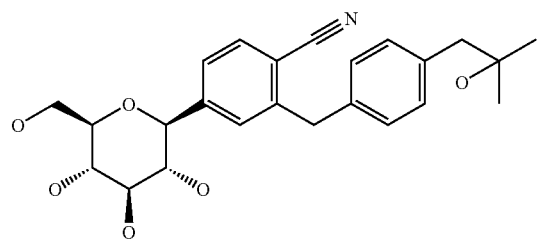 |
| 42 | 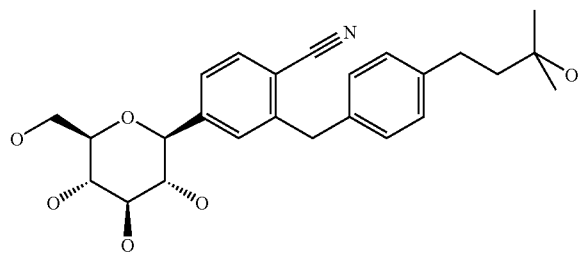 |
| 43 | 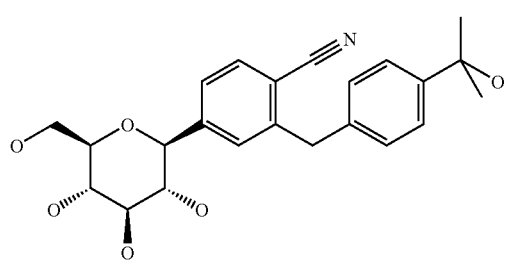 |

-continued
| Ex. | Structure |
|---|---|
| 44 | 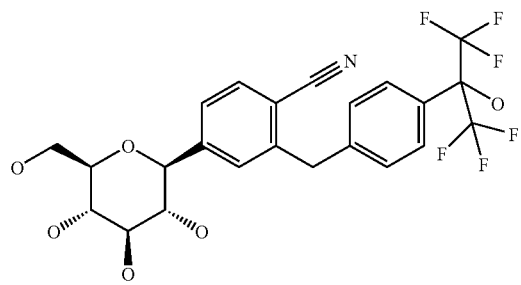 |
| 45 | 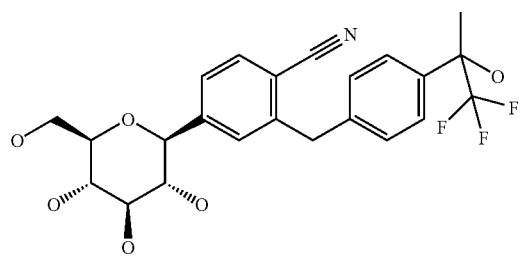 |
| 46 | 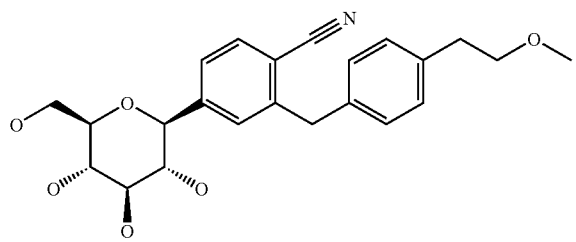 |
| 47 | 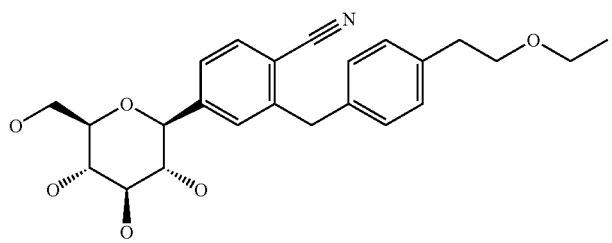 |
| 48 | 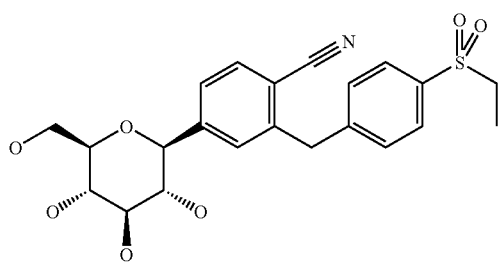 |

-continued

| Ex. | Structure |
|---|---|
| 49 | 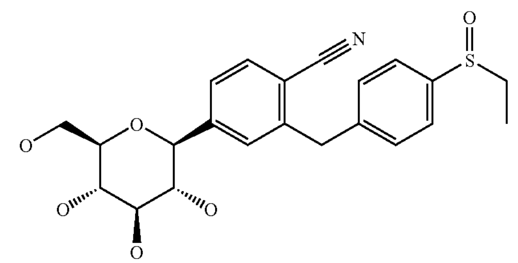 |
| 50 | 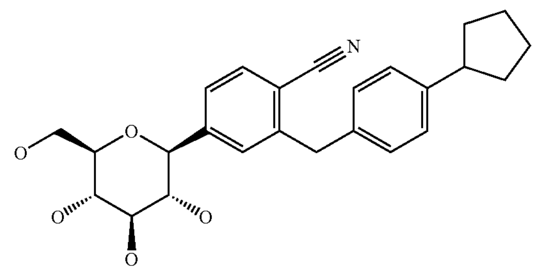 |
| 51 | 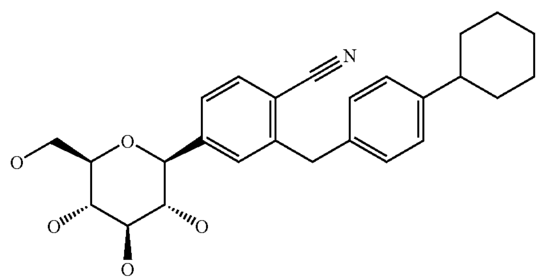 |

Some examples of formulations will now be described in which the term "active substance" denotes one or more compounds according to the invention, including the prodrugs or salts thereof. In the case of one of the combinations with one or additional active substances as described previously, the term "active substance" also includes the additional active substances.

EXAMPLE A

Tablets containing 100 mg of active substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE B

Tablets containing 150 mg of active substance
Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

| Hard gelatine capsules containing 150 mg of active substance Composition: 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

| Suppositories containing 150 mg of active substance Composition: 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

| Ampoules containing 10 mg active substance Composition: | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE F

| Ampoules containing 50 mg of active substance Composition: | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A glucopyranosyl-substituted benzonitrile derivative selected from the list according to formula II, III, or i.2,

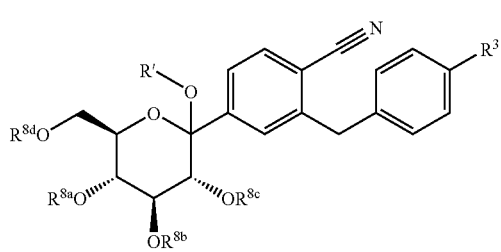

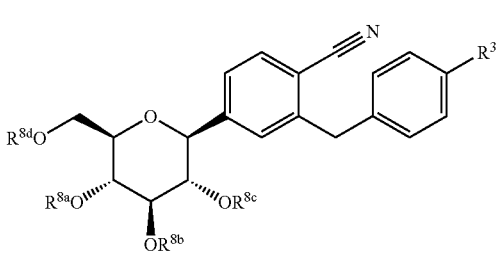

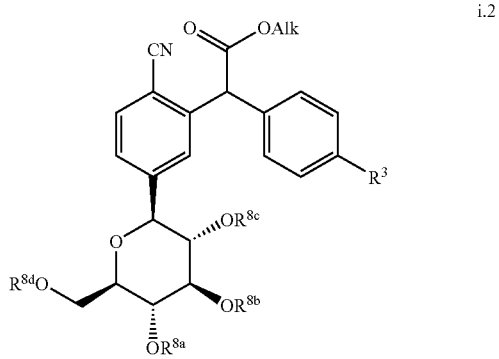

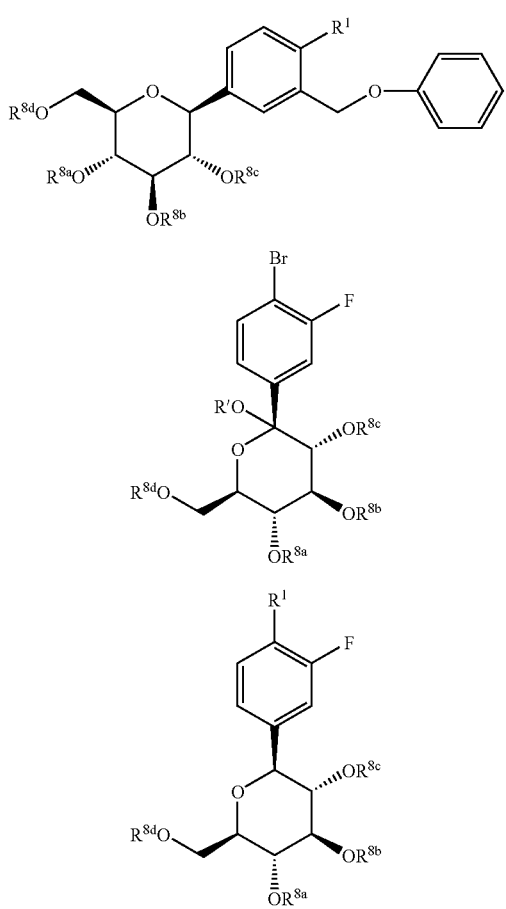

wherein

R³ is cyclopentyloxy, cyclobutyloxy, cyclohexyloxy, tetrahydropyran-4-yloxy, 1-acetyl-piperidin-4-yloxy or $C_{1-3}$-alkyloxy, and R' denotes H, $C_{1-4}$-alkyl, $(C_{1-18}$-alkyl)carbonyl, $(C_{1-18}$-alkyl)oxycarbonyl, arylcarbonyl or aryl-$(C_{1-3}$-alkyl)-carbonyl, wherein the alkyl or aryl groups may be mono- or polysubstituted by halogen;

$R^{8a}$, $R^{8b}$, $R^{8c}$, $R^{8d}$ independently of one another denote hydrogen or an allyl group, a benzyl group, a $(C_{1-4}$-alkyl)carbonyl, $(C_{1-4}$-alkyl)oxycarbonyl, arylcarbonyl, aryl-$(C_{1-3}$-alkyl)-carbonyl and aryl-$(C_{1-3}$-alkyl)-oxycarbonyl or a $R^aR^bR^c$Si group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and while alkyl, allyl, aryl and/or benzyl groups may be mono- or polysubstituted by halogen or $C_{1-3}$-alkoxy, and while benzyl groups may also be substituted by a di-$(C_{1-3}$-alkyl) amino group; and $R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups; and Alk denotes $C_{1-4}$-alkyl.

2. A glucopyranosyl-substituted benzonitrile derivative selected from the group consisting of:

(1) 2-(4-Cyclopentyloxy-benzyl)-4-(β-D-glucopyranos-1-yl)-benzonitrile, (2) 2-(4-Cyclobutyloxy-benzyl)-4-(β-D-glucopyranos-1-yl)-benzonitrile, (3) 2-(4-Cyclohexyloxy-benzyl)-4-(β-D-glucopyranos-1-yl)-benzonitrile, (4) 2-[4-(Tetrahydropyran-4-yloxy)-benzyl]-4-(β-D-glucopyranos-1-yl)-benzonitrile, (5) 2-[4-(1-Acetyl-piperidin-4-yloxy)-benzyl]-4-(β-D-glucopyranos-1-yl)-benzonitrile, (6) 2-(4-Methoxy-benzyl)-4-(β-D-glucopyranos-1-yl)-benzonitrile, (7) 2-(4-Ethoxy-benzyl)-4-(β-D-glucopyranos- 1-yl)-benzonitrile, (8) 4-(β-D-glucopyranos-1-yl)-2-(4-isopropoxy-benzyl)-benzonitrile, or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl.

3. Glucopyranosyl-substituted benzonitrile derivative according to claim 2, wherein the hydrogen atom of the hydroxyl group O-6 of the β-D-glucopyranosyl-group is replaced by a group selected from among $(C_{1-8}$-alkyl)carbonyl, $(C_{1-8}$-alkyl)oxycarbonyl and phenylcarbonyl.

4. Pharmaceutical composition, comprising a compound according to claim 2 optionally together with one or more inert carriers and/or diluents.

5. A method of treating diseases or conditions which can be influenced by inhibiting the sodium-dependent glucose cotransporter SGLT said method comprised of the steps of administering to a patient in need thereof a therapeutically effective amount of a compound according to claim 2, wherein said disease or condition is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia.

6. A method of treating metabolic disorders, said method comprised of the step of administering to a patient in need thereof a therapeutically effective amount of a compound according to claim 2, wherein said metabolic disorders is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia.

7. A method of inhibiting the sodium-dependent glucose cotransporter SGLT2, said method comprised of the step of administering to a patient in need thereof a therapeutically effective amount of a compound according to claim 2.

8. A method of treating the degeneration of pancreatic beta cells and/or for improving the functionality of beta cells, said method comprised of the step of administering to a patient in need thereof a therapeutically effective amount of a compound according to claim 2.

9. A method of slowing, delaying or treating diseases or conditions attributed to abnormal accumulation of liver fat, said method comprised of the step of administering to a patient in need thereof a therapeutically effective amount of a compound according to claim 2.

10. A glucopyranosyl-substituted benzonitrile derivative according to claim 1, wherein $R^3$ is methoxy, ethoxy or iso-propoxy.

11. A glucopyranosyl-substituted benzonitrile derivative according to claim 1, wherein said aryl groups are phenyl groups.

* * * * *